United States Patent
Hillukka et al.

(10) Patent No.: US 11,850,369 B2
(45) Date of Patent: Dec. 26, 2023

(54) MAPPING VARIABLE LOOP CATHETER HANDLE

(71) Applicant: St. Jude Medical, Cardiology Division, Inc., St. Paul, MN (US)

(72) Inventors: Brett A. Hillukka, Hanover, MN (US); Varun Bansal, Plymouth, MN (US); Evan Michael Leingang, Plymouth, MN (US); Richard A. Thompson, II, St. Louis Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1037 days.

(21) Appl. No.: 15/481,741

(22) Filed: Apr. 7, 2017

(65) Prior Publication Data

US 2017/0291008 A1 Oct. 12, 2017

Related U.S. Application Data

(60) Provisional application No. 62/320,067, filed on Apr. 8, 2016.

(51) Int. Cl.
*A61M 25/00* (2006.01)
*A61M 25/01* (2006.01)
(Continued)

(52) U.S. Cl.
CPC ......... *A61M 25/00* (2013.01); *A61B 18/1492* (2013.01); *A61M 25/008* (2013.01);
(Continued)

(58) Field of Classification Search
CPC ...... A61B 18/1492; A61B 2017/00323; A61B 2018/00196; A61B 2018/00357;
(Continued)

(56) References Cited

U.S. PATENT DOCUMENTS

| 6,068,629 A | 5/2000 | Haissaguerre et al. |
| D553,249 S | 10/2007 | Wakisaka et al. |

(Continued)

FOREIGN PATENT DOCUMENTS

| CN | 102000380 A | 4/2011 |
| CN | 103099675 A | 5/2013 |

(Continued)

OTHER PUBLICATIONS

International Search Report, Application No. PCT/US2017/026576, dated Jun. 20, 2017, 15 pages.

(Continued)

*Primary Examiner* — Linda C Dvorak
*Assistant Examiner* — Christine A Dedoulis
(74) *Attorney, Agent, or Firm* — Armstrong Teasdale LLP

(57) ABSTRACT

A catheter including a loop member adjustment mechanism for adjusting a diameter of a loop member is provided. The catheter further includes a longitudinally-extending catheter shaft including a proximal end portion and a distal end deflectable portion, wherein the distal end deflectable portion includes the loop member. The loop adjustment mechanism includes a loop member pull wire, wherein a distal end of the loop member pull wire is attached to the loop member, and a sliding member, located within the handle, wherein the sliding member is configured to translate within the handle, and wherein a proximal end of the pull wire is attached to the sliding member.

12 Claims, 28 Drawing Sheets

(51) Int. Cl.
*A61B 18/14* (2006.01)
*A61B 17/00* (2006.01)
*A61B 18/00* (2006.01)

(52) U.S. Cl.
CPC .... *A61M 25/0054* (2013.01); *A61M 25/0067* (2013.01); *A61M 25/0068* (2013.01); *A61M 25/0074* (2013.01); *A61M 25/0082* (2013.01); *A61M 25/0133* (2013.01); *A61M 25/0136* (2013.01); *A61M 25/0147* (2013.01); *A61B 2017/00323* (2013.01); *A61B 2018/00196* (2013.01); *A61B 2018/00357* (2013.01); *A61B 2018/00577* (2013.01); *A61B 2018/00839* (2013.01); *A61B 2018/1407* (2013.01); *A61M 2025/0163* (2013.01)

(58) Field of Classification Search
CPC A61B 2018/00577; A61B 2018/00839; A61B 2018/1407; A61B 2018/00952; A61B 2018/00946; A61B 2018/00202; A61B 5/6856; A61B 5/6855; A61B 5/6857; A61M 2025/0163; A61M 25/00; A61M 25/0054; A61M 25/0067; A61M 25/0068; A61M 25/0074; A61M 25/008; A61M 25/0082; A61M 25/0133; A61M 25/0136; A61M 25/0147
See application file for complete search history.

(56) References Cited

U.S. PATENT DOCUMENTS

| | | | |
|---|---|---|---|
| D581,052 S | 11/2008 | Root et al. | |
| 8,092,424 B2 * | 1/2012 | Mueller | A61M 5/321 604/110 |
| D715,429 S | 10/2014 | Yu et al. | |
| D718,437 S | 11/2014 | Osypka | |
| 8,906,051 B2 | 12/2014 | Mitelberg et al. | |
| 8,945,059 B2 | 2/2015 | Loewen | |
| D726,906 S | 4/2015 | Reed | |
| D726,908 S | 4/2015 | Yu et al. | |
| 8,998,844 B2 | 4/2015 | Reed | |
| 9,011,382 B2 | 4/2015 | Nilsson et al. | |
| D733,874 S | 7/2015 | Yu et al. | |
| D734,457 S | 7/2015 | Yu et al. | |
| D751,194 S | 3/2016 | Yu et al. | |
| 2006/0241366 A1 * | 10/2006 | Falwell | A61B 5/287 600/374 |
| 2007/0225641 A1 * | 9/2007 | Schneider | A61M 25/0136 604/93.01 |
| 2009/0264759 A1 * | 10/2009 | Byrd | A61B 8/445 600/445 |
| 2010/0325296 A1 | 12/2010 | Hamasaki et al. | |
| 2011/0054287 A1 * | 3/2011 | Schultz | A61B 5/0422 600/374 |
| 2011/0054446 A1 | 3/2011 | Schultz | |
| 2011/0264074 A1 | 10/2011 | Tegg et al. | |
| 2012/0143088 A1 | 6/2012 | Schultz | |
| 2013/0123691 A1 | 5/2013 | Schultz | |
| 2013/0158379 A1 * | 6/2013 | Selkee | A61B 5/287 604/95.04 |
| 2014/0207185 A1 | 7/2014 | Groble et al. | |
| 2014/0336573 A1 | 11/2014 | Yu et al. | |
| 2015/0057610 A1 * | 2/2015 | Osypka | A61M 25/0136 604/95.04 |

FOREIGN PATENT DOCUMENTS

| | | |
|---|---|---|
| CN | 104434307 A | 3/2015 |
| CN | 105188827 A | 12/2015 |
| EP | 2594308 A1 | 5/2013 |
| WO | 2007001981 A2 | 1/2007 |
| WO | 2010048676 A1 | 5/2010 |
| WO | 2015125366 | 8/2015 |

OTHER PUBLICATIONS

International Report on Patentability for International Patent Application No. PCT/US2017/026576, dated Oct. 18, 2018, 9 pages.

* cited by examiner

MAPPING VARIABLE LOOP CATHETER HANDLE

CROSS-REFERENCE TO RELATED APPLICATIONS

This application claims the benefit of U.S. Provisional Patent Application No. 62/320,067, filed Apr. 8, 2016, the contents of which are hereby incorporated by reference herein in their entirety.

FIELD

The present disclosure relates generally to medical devices that are used in the human body. In particular, in many embodiments, the present disclosure relates to a catheters and catheter handles, such as unidirectional and/or bidirectional mapping variable loop catheter handles, capable of deflecting a distal portion of a catheter shaft in at least one direction and also adjusting the diameter of the loop at the distal portion of the catheter shaft to improve overall performance and maneuverability of the catheter shaft and loop during a procedure.

BACKGROUND

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. These lesions disrupt undesirable cardiac activation pathways and thereby limit or prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal tip can be deflected by a pull wire attached at the distal end of the catheter and extending proximally to an actuator in a control handle that controls the application of tension on the pull wire. In many cases, the distal tip of the catheter may include a loop member (or spiral loop member) to further diagnostic and treatment application.

BRIEF SUMMARY OF THE DISCLOSURE

In one embodiment, the present disclosure is directed to a catheter including a loop member adjustment mechanism for adjusting a diameter of a loop member. The catheter further includes a longitudinally-extending catheter shaft including a proximal end portion and a distal end deflectable portion, wherein the distal end deflectable portion includes the loop member, a handle attached to the proximal end portion of the catheter shaft, and a deflection mechanism positioned inside the handle and including a pull wire for deflecting the distal end deflectable portion of the catheter shaft. The loop adjustment mechanism includes a loop member pull wire, wherein a distal end of the loop member pull wire is attached to the loop member, and a sliding member, located within the handle, wherein the sliding member is configured to translate within the handle, and wherein a proximal end of the pull wire is attached to the sliding member.

In another embodiment, the present disclosure is directed to a deflecting and sizing apparatus for a catheter handle including a catheter shaft having a distal end deflectable portion including a loop member. The apparatus includes a deflection mechanism positioned inside the handle and including a pull wire for deflecting the distal end deflectable portion of the catheter shaft, and a loop member adjustment mechanism for adjusting a diameter of the loop member. The loop member adjustment mechanism includes a loop member pull wire, wherein a distal end of the loop member pull wire is attached to the loop member, and a sliding member, located within the handle, wherein the sliding member is configured to translate within the handle, and wherein a proximal end of the pull wire is attached to the sliding member.

In another embodiment, the present disclosure is directed to a method of adjusting the diameter of a loop member on a catheter shaft of a catheter. The method comprises providing a catheter including a longitudinally-extending catheter shaft including a proximal end portion and a distal end deflectable portion, wherein the distal end deflectable portion includes the loop member, a handle attached to the proximal end portion of the catheter shaft, a deflection mechanism positioned inside the handle and including a pull wire for deflecting the distal end deflectable portion of the catheter shaft, and a loop adjustment mechanism including a loop member pull wire. A distal end of the loop member pull wire is attached to the loop member, and a sliding member, located within the handle, wherein the sliding member is configured to translate within the handle, and wherein a proximal end of the pull wire is attached to the sliding member.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
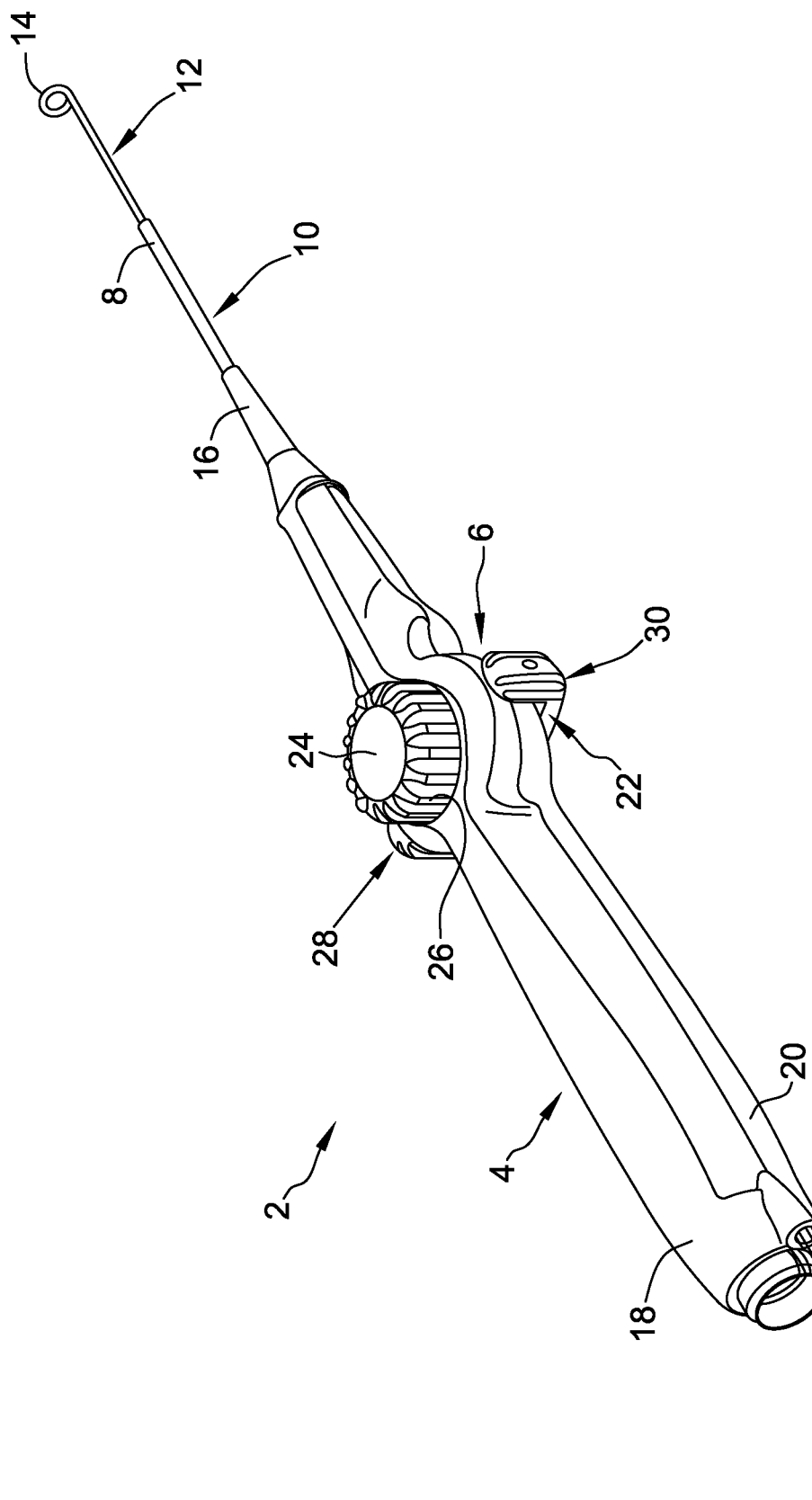
FIG. 1 is an isometric view of a catheter including a catheter handle and steering actuator for deflecting a catheter shaft.

The present disclosure provides medical devices including catheter systems, catheters, and catheter handles suitable for use in the human vasculature for known medical procedures. Catheter systems, catheters, and catheter handles of the multiple embodiments of the present disclosure include a loop member, such as a circular loop member or other shaped loop member, on a distal end portion of a catheter shaft along with a loop member adjustment mechanism located in and/or on the catheter handle that allows a user to adjust (increase and/or decrease) the diameter of the loop member before, during, or after a procedure in the vasculature of a patient. In many embodiments of the present disclosure, the loop member adjustment mechanism includes a loop member pull wire wherein a proximal end of the loop member pull wire is attached to a sliding member located inside the catheter handle. This sliding member is configured to interface (i.e., through the use of interfacing gears) with a rotating knob located on the exterior of the catheter handle to allow for increasing/decreasing the diameter of the loop member. In other embodiments of the present disclosure, the proximal end of the loop member pull wire is attached to a gear assembly located inside of the catheter handle that is configured to interface with a sliding mechanism located on the exterior of the catheter handle to allow for increasing/decreasing the diameter of the loop member. The disclosed embodiments may lead to more consistent and improved patient outcomes, as well as a reduced amount of fatigue for the user. For purposes of this description, the present disclosure will be generally described in connection with numerous embodiments of a bidirectional catheter including a circular loop member. It is contemplated, however, that the described features and methods of the present disclosure as described herein may be incorporated into any number of bidirectional or other catheters such as unidirectional catheters, or other medical devices having a loop member of another shape (oval, etc.) as would be appreciated by one of ordinary skill in the art based on the disclosure herein.

In many embodiments of the present disclosure, the loop member adjustment mechanism located in the catheter handle that allows a user to adjust (increase and/or decrease) the diameter of the loop member will include a braking mechanism such that upon the decreasing of the diameter of the loop member (i.e., closing the loop member) the braking mechanism will hold or otherwise affix the loop member pull wire in the desired position to maintain the diameter adjustment. Because the natural state of the loop member is open, or in the largest diameter, when the diameter of the loop member is decreased, a natural tension is imposed on the loop member pull wire such that it wants to return to its natural, or open, position. The braking mechanism as described herein allows a user to "lock" or otherwise hold the desired position of the loop member for a desired time period without additional force or effort. Because the "locking" feature does not permanently fix the loop member pull wire in a particular position, this feature is reversible upon releasing tension on the loop pull wire (by rotating the proximal knob on the handle to move the sliding member distally). The disclosed embodiments herein may lead to more consistent and improved patient outcomes, as well as a reduced amount of fatigue for the user, as noted.

The deflecting and sizing apparatuses described herein for catheter systems, catheters, and catheter handles provide a number of advantages and improvements. By allowing an operator to easily and reliably adjust the diameter of the loop member on the distal tip of the catheter shaft during a procedure (as opposed to selecting a single, non-adjustable size prior to the procedure), the operator can more easily maneuver the catheter shaft through the tortuous vasculature of a patient during a procedure, irrespective of the size of the artery of the patient. Additionally, adjustability of the diameter of the loop member may result in the loop member staying in better direct contact with the artery walls (in a circular pattern) during a procedure; that is, because the diameter of the loop member may be increased/decreased during a procedure, such as a cardiac ablation procedure, the size of the loop member can be customized to remain in direct contact with the artery to ensure a more uniform ablation, and hence a more desirable outcome.

Referring now to FIG. 1, there is shown an isometric view of a conventional bidirectional catheter 2 including a catheter handle 4 having a steering actuator 6 for deflecting a catheter shaft 8, which includes proximal end portion 10, and distal end deflectable portion 12 including loop member 14, and is supported by strain relief 16. Distal end deflectable portion 12 of catheter shaft 8 may be deflectable in one or two directions as described herein. As further illustrated in FIG. 1, catheter handle 4 includes an upper handle housing 18 and a lower handle housing 20. Steering actuator 6 is pivotally sandwiched between upper handle housing 18 and lower handle housing 20, and includes an outer actuator 22 and an outer knob 24, which may include ridges 26. Outer actuator 22 defines a first boss 28 and a second boss 30 that a user (e.g., an electrophysiologist or other clinician) uses to effect deflection of distal end deflectable portion 12 of catheter shaft 8.

Figure 2:
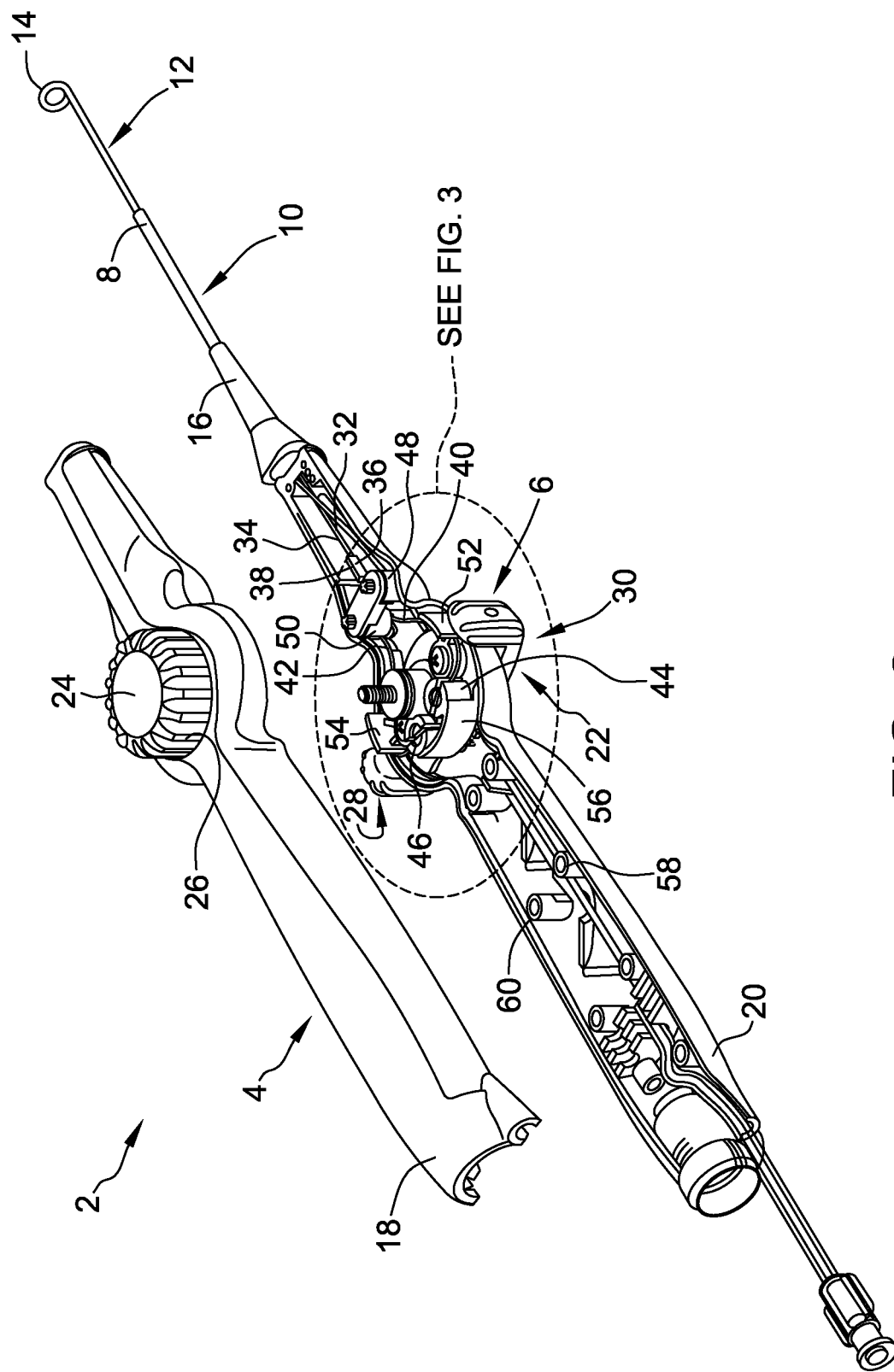
FIG. 2 is an isometric view of the catheter of FIG. 1 with the upper handle housing exploded away from the handle to reveal internal components of the steering actuator.

Referring now to FIG. 2, there is shown bidirectional catheter 2 including catheter handle 4 and steering actuator 6 as shown in FIG. 1, but with upper handle housing 18 exploded away from lower handle housing 20 and the rest of catheter handle 4, thus revealing internal components of steering actuator 6. As illustrated, the proximal end of catheter shaft 8 is supported by strain relief 16. Pull wires 32 and 34 (both also illustrated in FIG. 4 as described below), which extend from catheter handle 4 down catheter shaft 8 to an anchor point (not shown) in distal end deflectable portion 12 of catheter shaft 8, enter catheter handle 4 from its distal end. In this embodiment, each pull wire 32 and 34 is then attached by crimp 36 and 38, to fibers 40 and 42 that extends from crimps 36 and 38 to a respective anchor point 44 and 46 (e.g., a tensioning mechanism, embodiments of which are described more fully below). Fibers 40 and 42 comprise a durable material that is selected to handle the circuitous path (and concomitant stresses) that fibers 40 and 42 follow from crimps 36 and 38 to anchor point 44 and 46.

Each fiber 40 and 42 passes over a roller 48 and 50 (or pull-wire-deflection surface), then passes around a wall section (or guide wall or pull wire guide wall) 52 and 54 before reaching one of the anchor points 44 and 46. In one embodiment as shown in FIG. 2, the wall sections (or guide walls) 52 and 54 comprise arc wall sections or "wing wall" sections. These wall sections increase the length of the path traversed by fibers 40 and 42 (or a pull wire 32 and 34) after passing rollers 48 and 50 on its way to the mounting point of the proximal portion of fibers 40 and 42. Further illustrated are rear wall section 56 and guide posts 58 and 60 (See also FIG. 3 discussed below).

Figure 3:
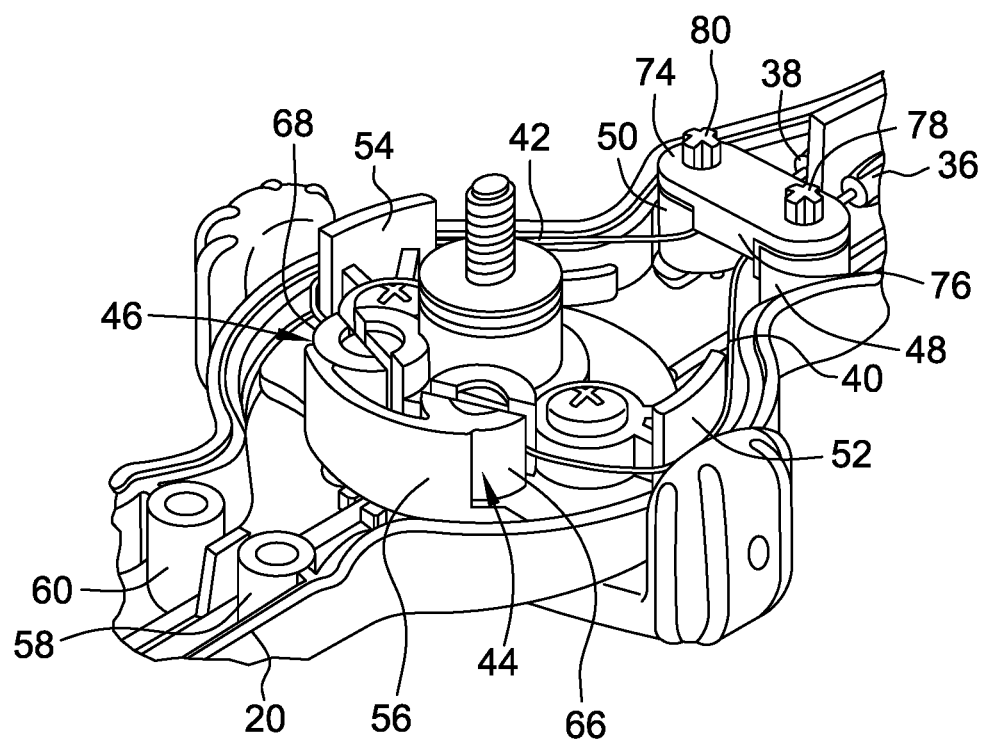
FIG. 3 is an enlarged view of the circled portion of FIG. 2.
Figure 4:
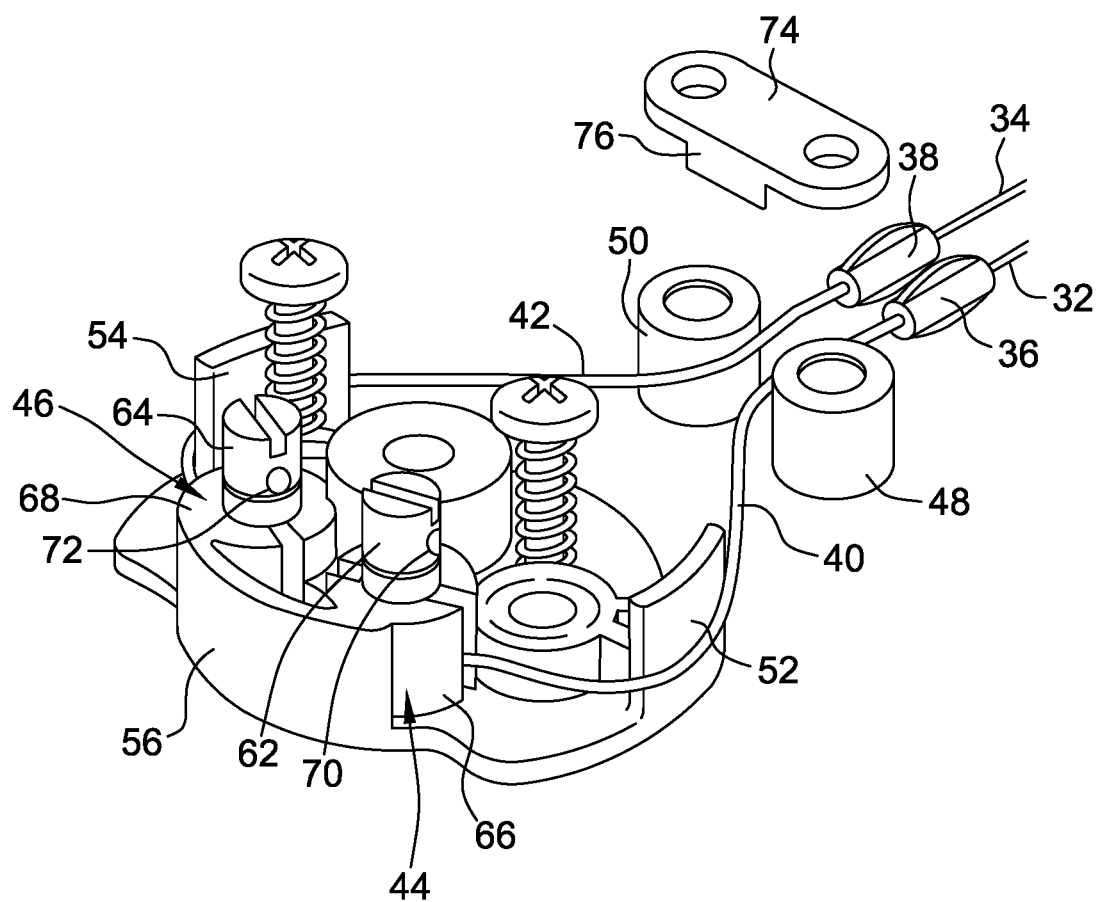
FIG. 4 is similar to FIG. 3 and depicts various components of the steering actuator spread apart to make it easier to see various aspects of the construction.

Referring now to FIGS. 3 and 4, further details of a representative inner actuator and the various components that it supports are described. FIGS. 3 and 4 are fragmentary, isometric views of the portion of catheter handle 4 and steering actuator 6 in the dashed circle in FIG. 2. Starting at the upper right portion of these Figures, there is shown two crimps 36 and 38 that connect the first and second pull wires 32 and 34 (shown in FIG. 4 but not FIG. 3) to fibers 40 and 42. Each fiber 40 and 42 then extends around rollers 48 and 50 before passing around wall sections 52 and 54 and then to an anchor points 44 and 46.

In this embodiment, each anchor point 44 and 46 comprises a pull wire tensioning or tension mechanism (e.g., a pull wire "tuner mechanism" or a pull wire termination) that, in one embodiment, includes tension adjustment pins 62 and 64 (e.g., a "tuning pin") (shown in FIG. 4) and a pin blocks 66 and 68. As further shown in FIGS. 3 and 4, each tension adjustment pin 62 and 64 may be rotated into its respective pin block 66 and 68. Tension adjustment pins 62 and 64 and pin blocks 66 and 68 may include screw threads. That is, both tension adjustment pins 62 and 64 and pin blocks 66 and 68 comprising a tensioning mechanism may be threaded, or either tension adjustment pins 62 and 64 or pin blocks 66 and 68 comprising a tensioning mechanism may be threaded, or neither tension adjustment pins 62 and 64 nor pin blocks 66 and 68 comprising a tensioning mechanism may be threaded.

In the embodiment depicted in FIGS. 3 and 4, pin blocks 66 and 68 each comprise a slotted pillar. In particular, each pin block 66 and 68 comprises a hollow cylinder with a slot or cut through opposing locations of the cylinder wall, the cut also passing through the center of the pillar. As may be seen in FIG. 4, each tension adjustment pin 62 and 64 includes a fiber channel or hole 70 and 72. Each fiber 40 and 42 is connected to the tensioning mechanism by inserting a proximal portion of the fiber into the corresponding fiber channel or hole 70 and 72 in tension adjustment pins 62 and 64, and then rotating tension adjustment pins 62 and 64 in pin blocks 66 and 68, which traps fibers 40 and 42 between the outer surface of tension adjustment pins 62 and 64 and the inner surface of pin block 66 and 68. The slots in the cylindrical walls of pin blocks 66 and 68 allow the walls to flex slightly as fibers 40 and 42 are wound onto a respective tension adjustment pin 62 and 64. This allows fibers 40 and 42, and thus pull wires 32 and 34, to be preloaded with a desired tension. This system simplifies manufacturing by allowing for less precise initial trimming of the fibers (or pull wires) since adjustments can be made via the tensioning mechanisms. The tensioning mechanisms allow for easy termination of the fiber ends and permit precise preloading of desired tension on the pull wires. Rear wall section 56 helps support the tensioning mechanisms.

Also illustrated in FIGS. 3 and 4, is roller retention cap 74 that includes a guide wall 76 that extends downwardly to keep fibers 40 and 42 at a desired trajectory toward wall sections 52 and 54. Each roller pin 78 and 80 (as shown in FIG. 3) has a cross-sectional area in the shape of a cross, for example, rather than a circle. This cross-sectional shape for roller pins 78 and 80 helps reduce friction between the outer surface of roller pins 78 and 80 and the inner surface of the rollers 48 and 50. It should be noted that each roller 48 and 50 may be replaced with a fixed cylinder that does not rotate on a roller pin, or by an arcuate guiding surface configured to guide one of the fibers on the desired trajectory toward its respective wall sections. It should also be kept in mind that each of the pull wires could traverse the entire course from its anchor point at the distal end of the catheter to its anchor point in the handle (e.g., at one of the tensioning mechanisms shown in FIGS. 3 and 4).

Bidirectional catheter 2 including catheter handle 4 having steering actuator 6, catheter shaft 8 and loop member 14, as illustrated in FIGS. 1-4 as described above, may further include a loop member adjustment assembly or mechanism for allowing an operator to adjust the diameter of loop member 14; that is, an assembly or mechanism to increase or decrease the diameter of loop member 14. This diameter adjustment of loop member 14 may be done at any time during a procedure, and may further be done with or without deflection of distal end deflectable portion 12 of catheter shaft 8; that is, any deflection of distal end deflectable portion 12 is independent of any diameter adjustment of loop member 14 in accordance with the present disclosure. This independent adjustment is achieved in the present disclosure through the use of multiple pull wires contained within bidirectional catheter 2 as described below. By having the capability to adjust the diameter of loop member 14 before or during a procedure, an operator may be able to more effectively navigate the vasculature of a patient as described herein and improve patient outcomes as noted above.

Figure 5:
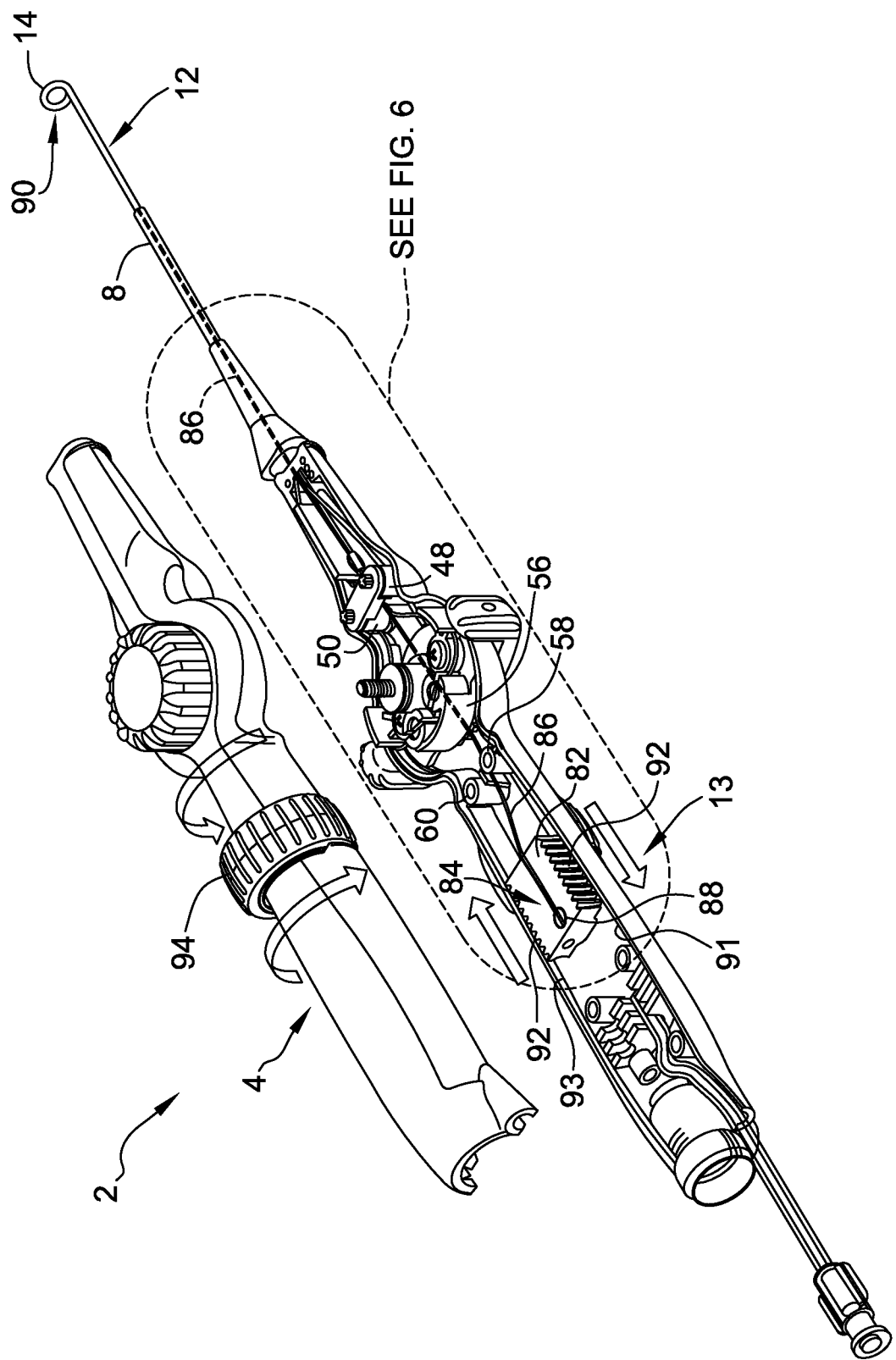
FIG. 5 is an isometric view of a catheter with the upper handle housing exploded away from the handle to review internal components including a sliding member, rotating knob, and loop member pull wire.

In some embodiments of the present disclosure, as illustrated in FIG. 5, bidirectional catheter 2 includes a loop member adjustment mechanism 13. Loop member adjustment mechanism 13 includes a sliding member 82 that is sized and configured to fit inside of catheter handle 4 and along inner catheter handle walls 91 and 93 of catheter handle 4 to allow for the adjustment of the diameter of loop member 14, as further described herein. Inner catheter handle walls 91 and 93 may guide sliding member 82 to allow sliding member 82 to remain in its desired position and conformation to allow for proper alignment of sliding member 82 within catheter handle 4. By keeping sliding member 82 properly aligned within catheter handle 4, any potential for the binding or misalignment of sliding member 82 is reduced or eliminated. Sliding member 82 is attached to a proximal portion 84 of loop member pull wire 86 via tension adjustment pin 88. A distal portion 90 of loop member pull wire 86 is attached at an attachment point (not shown in FIG. 5) to loop member 14 located on distal end deflectable portion 12 of catheter shaft 8. Loop member pull wire 86 is routed through catheter handle 4 from tension adjustment pin 88 to the attachment point (not shown in FIG. 5) between guide posts 58 and 60, under rear wall section 56, and between rollers 48 and 50 (See also FIG. 6). In the embodiment illustrated in FIG. 5, sliding member 82 includes gears (or grooves or ridges) 92 such that sliding member 82 is configured to interface with a rotating knob 94 that includes gears on its underside (not shown in FIG. 5) located on catheter handle 4. In some embodiments, rotating knob 94 may include a friction increasing cover (not shown in FIG. 5) thereon to increase the grip capability of rotating knob 94 during use. The friction increasing cover, which may also keep unwanted contaminants from entering catheter handle 94 by sealing rotating knob 94 on catheter handle 4, may be comprised of any suitable material that increases grip friction including, for example, a silicone material.

When sliding member 82 is connected to rotating knob 94 and rotating knob 94 is turned clockwise (looking from the proximal end of catheter handle 4), loop member pull wire 86 is pulled proximally with respect to catheter handle 4 and the diameter of loop member 14 is decreased to a desired amount. The more that rotating knob 94 is turned clockwise, the more the diameter of loop member 14 is decreased. With this embodiment, the diameter of loop member 14 may be adjusted (i.e., increased or decreased) independent of any deflection of distal end deflectable portion 12 of catheter shaft 8. As will be recognized by one skilled in the art based on the disclosure herein, rotating knob 94 and sliding member 82 could be sized and configured such that as rotating knob 94 is turned counterclockwise the diameter of loop member 14 is decreased.

Figure 6:
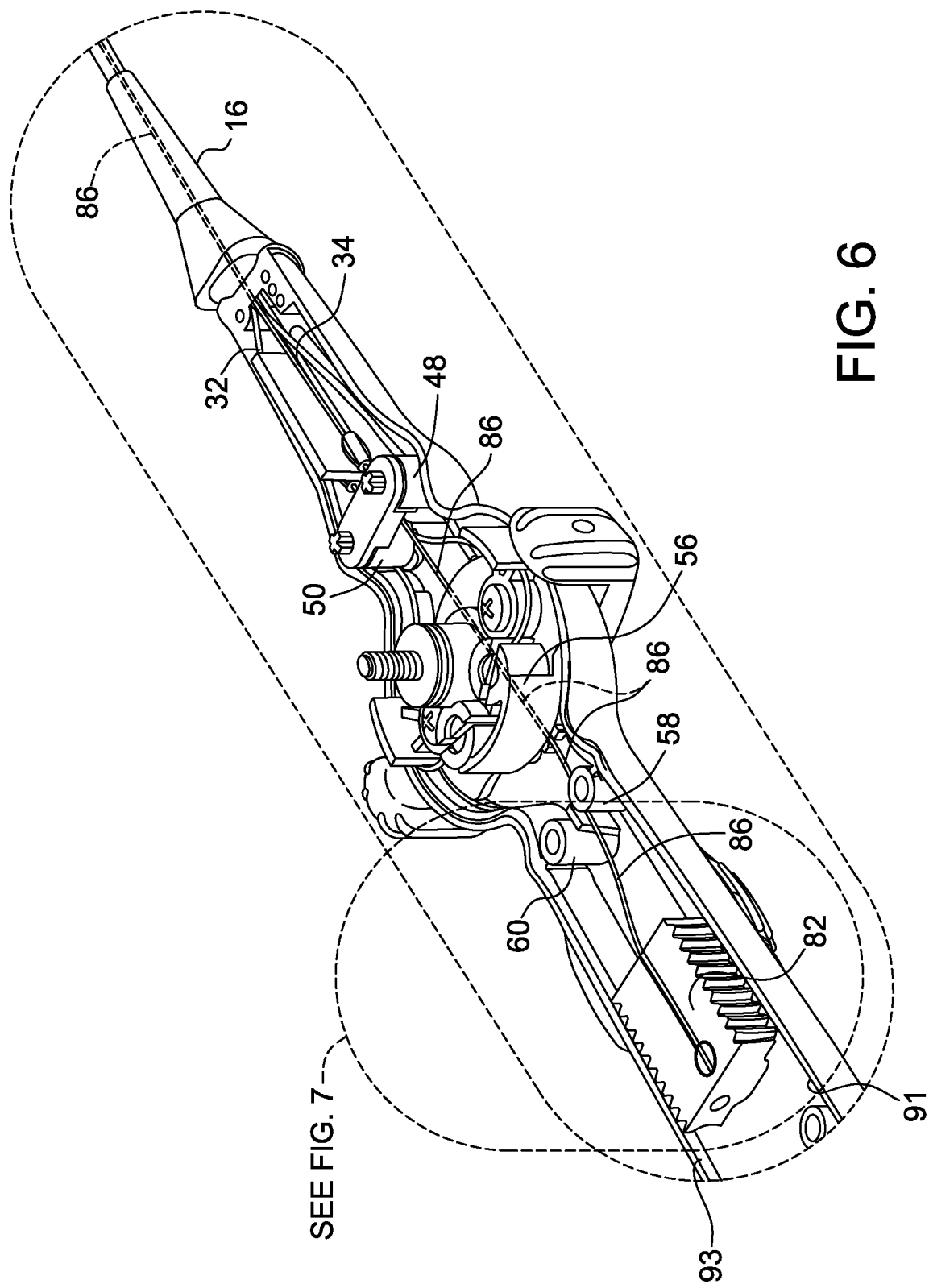
FIG. 6 is an enlarged view of the circled portion of FIG. 5.

Referring now to FIG. 6, there is shown an enlarged view of the circled portion in FIG. 5 to further illustrate the location of loop member pull wire 86 within catheter handle 4 as well as its path from sliding member 82, between guide posts 58 and 60, under rear wall section 56 and through rollers 48 and 50. As noted herein, loop member pull wire 86 is independent of pull wires 32 and 34 and solely controls the diameter adjustment of loop member 14 (not shown in FIG. 6 but see FIG. 5). In one embodiment as shown in FIG. 6, loop member pull wire 86 is fed between guide posts 58 and 60, under rear wall section 56 and between rollers 48 and 50 such that it is ultimately fed through strain relief 16 and into loop member 14 (not shown in FIG. 6) to an attachment point therein (not shown in FIG. 6).

Figure 7:
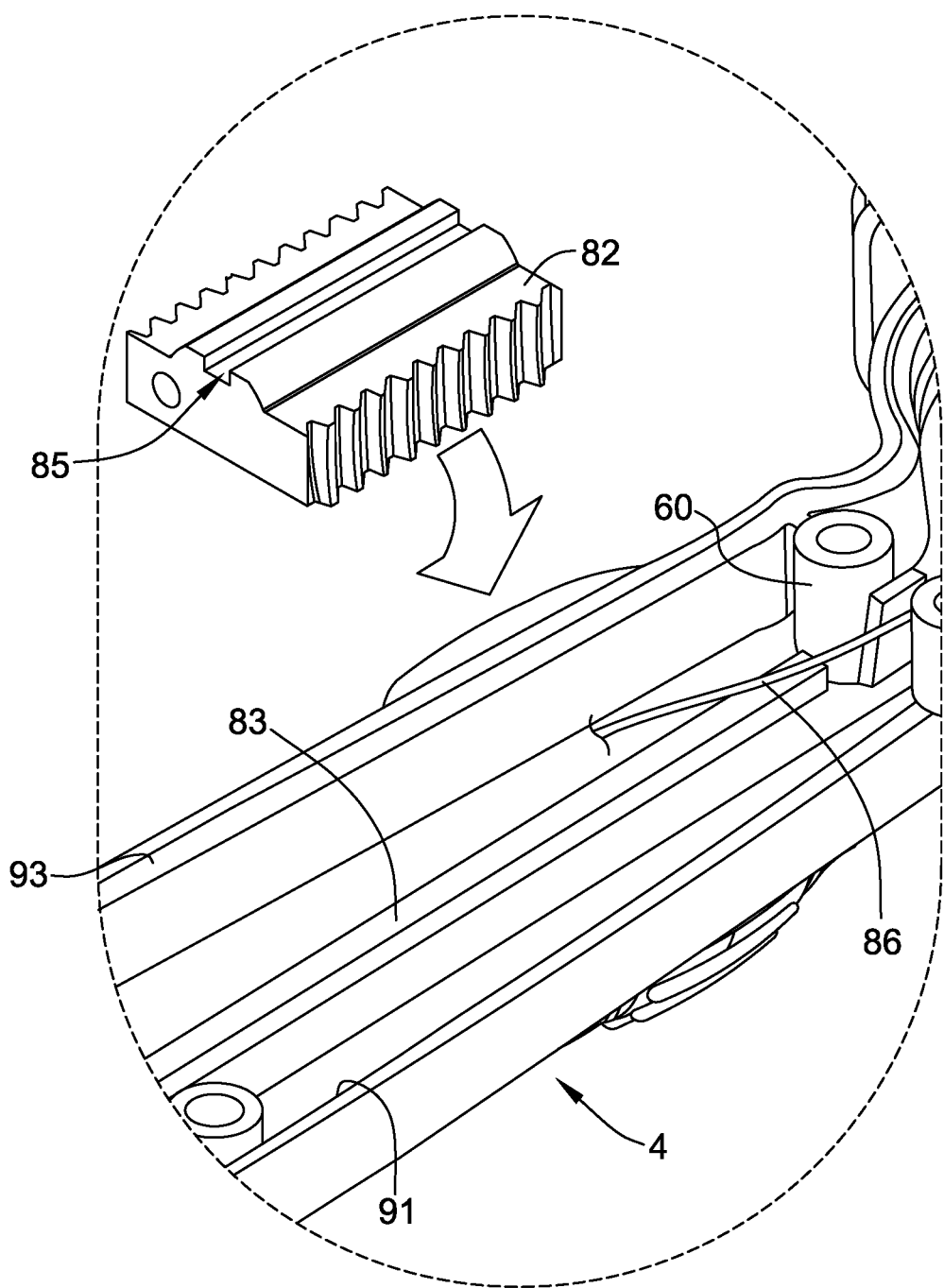
FIG. 7 is an enlarged view of the circled portion of FIG. 6.

In an alternative embodiment of the present disclosure, catheter handle 4 (as shown in FIG. 5 and further illustrated in FIG. 7, which enlarges the circled portion of FIG. 6), may optionally include further means for maintaining sliding member 82 in proper alignment within catheter handle 4 during use thereof. As noted above, by keeping sliding member 82 properly aligned within catheter handle 4 during movement therein, any chance for sliding member 82 to bind or pinch or otherwise have the desired sliding path compromised within catheter handle 4 is reduced or eliminated. As such, the overall device is more user friendly and performs more consistently. As shown in FIG. 7, wherein sliding member 82 is exploded away and rotated 180 degrees with respect to catheter handle 4, catheter handle 4 may include in some embodiments a center guide channel 83 sized and configured to slidably attach to a groove 85 located on sliding member 82. When slidably attached to groove 85 on sliding member 82, center guide channel 83 guides sliding member 82 along the desired path within catheter handle 4 and assists in keeping sliding member 82 moving in a straight line within catheter handle 4 to reduce or eliminate any potential for binding of sliding member 82 within catheter handle 4. Another center guide channel (not shown in FIG. 7) may also be present on the top of catheter handle 4 and sized and configured to slidably attach to a second groove (not shown in FIG. 7) located on the top of sliding member 82 such that sliding member 82 is guided along the desired path within catheter handle 4 through the use of two separate grooves and center guide channels.

The catheters and catheter handles described herein and including a loop member adjustment assembly or mechanism, such as a sliding member and rotating knob as described above, for adjusting the diameter of the loop member using a loop member pull wire may optionally include in some embodiments a locking or braking mechanism to effectively "lock" or "hold" the sliding member as described herein in a desired location (i.e., after the diameter of the loop member has been reduced and there is tension on the loop member pull wire) until a sufficient force is utilized to overcome the "lock" or "hold" (i.e., the operator rotates the rotating knob to increase the diameter of the loop member and release some or all of the tension on the loop member pull wire). This locking or braking mechanism may be desirable in some embodiments as the natural state of the loop member is "open" (i.e., the diameter is at its largest such that a force is required to reduce the diameter). In some embodiments, a threaded pitch may be used between the rotating knob and the sliding member to provide a locking or braking mechanism. In other embodiments, a friction ring or friction member may be introduced between the sliding member and the handle, and/or between the rotating knob and the sliding member and/or between the rotating knob and the handle body to produce a frictional resistance between the components and provide a frictional drag for locking or holding. In some embodiments, a combination of a threaded pitch and a friction ring or friction member may be utilized to provide the desired amount of locking or braking.

In many embodiments, a friction ring or friction member is a desirable method for providing a locking or holding feature. The friction ring or member may be comprised of a thermoplastic material, for example, and may be in the form of a block, plug, ring, overlay or the like that is optionally secured to the exterior surface of the threaded portion of the sliding member, the interior or exterior of the handle, the threaded or unthreaded portion of the rotating knob, or any combination thereof. In some embodiments of the present disclosure, the friction ring or member is formed of silicone, polytetrafluoroethylene, polyurethane, copolymers of hexafluoropropylene and vinylidene fluoride, or combinations thereof. In one particular embodiment of the present disclosure, the friction ring or member is formed of about 85% by weight silicon and about 15% by weight polytetrafluoroethylene. The friction ring or member may be sized and configured to provide the desired amount of friction resistance or "locking" for each desired application. In some embodiments, two or more friction rings or members may be used in combination wherein the friction rings or members have different coefficients of friction.

Figure 8:
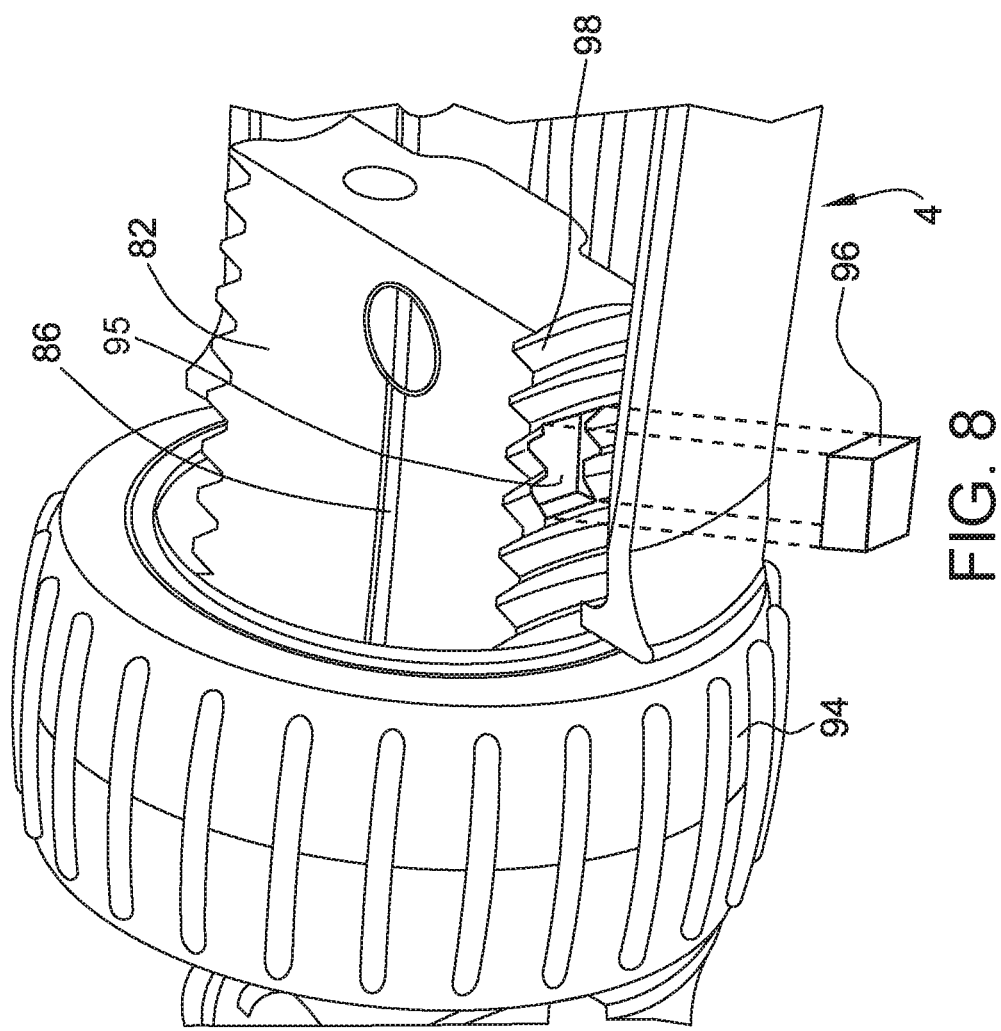
FIG. 8 is a partial cut away view of a portion of a catheter handle to show a braking mechanism between a rotating knob and a sliding member.

Referring now to FIG. 8, there is shown a specific embodiment of the present disclosure wherein the bidirectional catheter includes a friction member for providing a frictional resistance and therefore a "locking" feature as described above to improve the performance of the device. FIG. 8 is a partial cut away view of a portion of a catheter handle to show a braking mechanism embedded in the sliding member for frictional engagement with the rotating knob. As illustrated in FIG. 8, sliding member 82 located in catheter handle 4 and in rotating connection with rotating knob 94 includes friction member 96 sized and configured for insertion into a pocket 95 located within gear teeth 98. Friction member 96 is positioned in gear teeth 98 (i.e., molded therein, adhered thereto, etc.) of sliding member 82 such that friction member 96 will contact and interact with the gears (not shown) of rotating knob 94 during use and provide the desired "locking" feature as tension is created on loop member pull wire 86.

Figure 9:
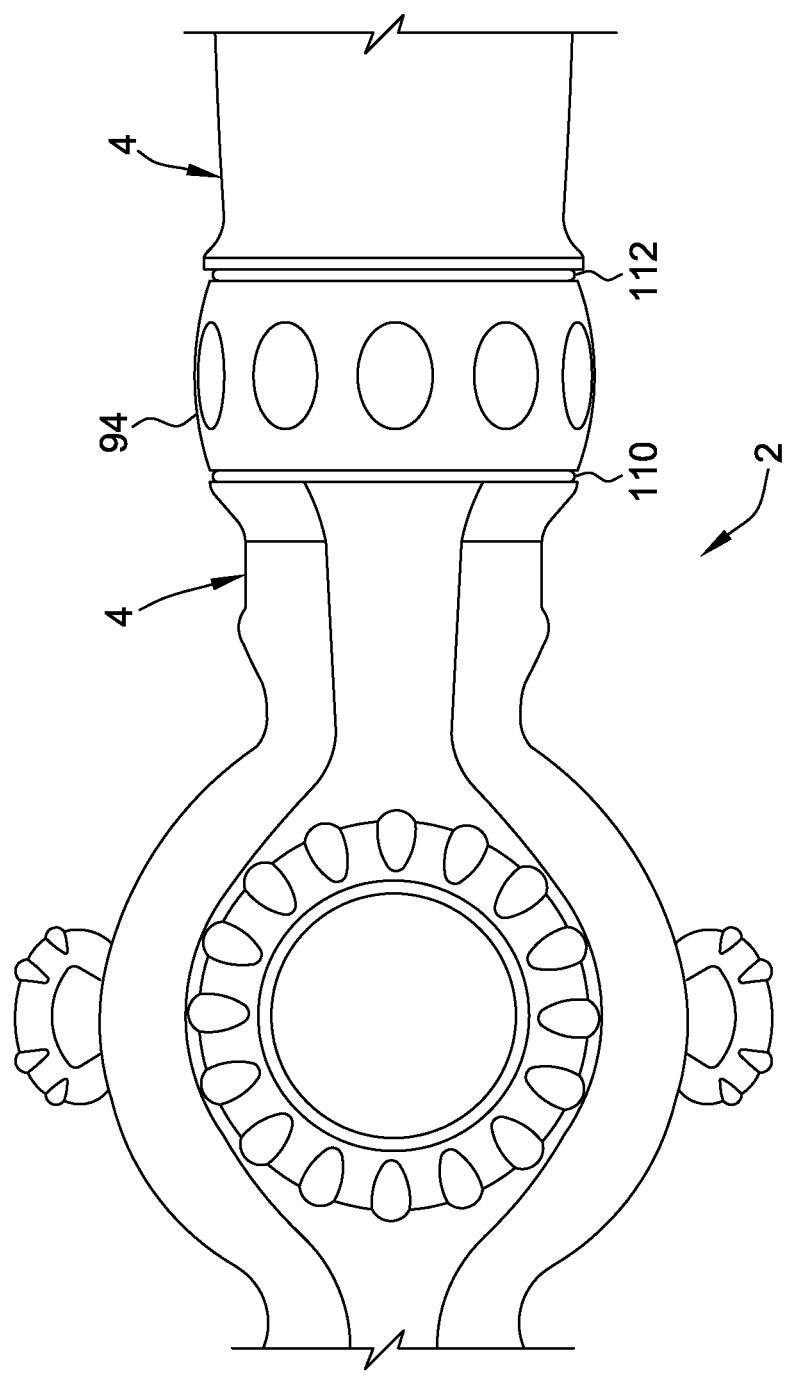
FIG. 9 is an isometric view of a catheter including a catheter handle and rotating knob including two locking friction rings.

In another embodiment the bidirectional catheter includes one or more locking friction rings located between the rotating knob and catheter handle, which in some embodiments may provide a variable locking function to the rotating knob. Referring now to FIG. 9, there is shown catheter 2 including catheter handle 4 and rotating knob 94. Catheter 2 additionally includes distal locking ring 110 located distal rotating knob 94 and proximal locking ring 112 located proximal rotating knob 94. Distal locking ring 110 results in the locking force applied to rotating knob 94 increasing as rotating knob 94 is turned more and more for adjusting the diameter of the loop member (not shown in FIG. 9) and allows the starting of the turning of rotating knob 94 to be at a lower force while providing locking throughout the turning cycle. Proximal locking ring 112 results in the locking force applied to rotating knob 94 to decrease as rotating knob 94 is turned more and more for adjusting the diameter of the loop member. Although illustrated in FIG. 9 as having both a distal locking ring 110 and a proximal locking ring 112, it will be recognized that catheter 2 may include only a distal locking ring 110, only a proximal locking ring 112, or both a distal locking ring 110 and a proximal locking ring 112 as illustrated in FIG. 9.

Figure 10:
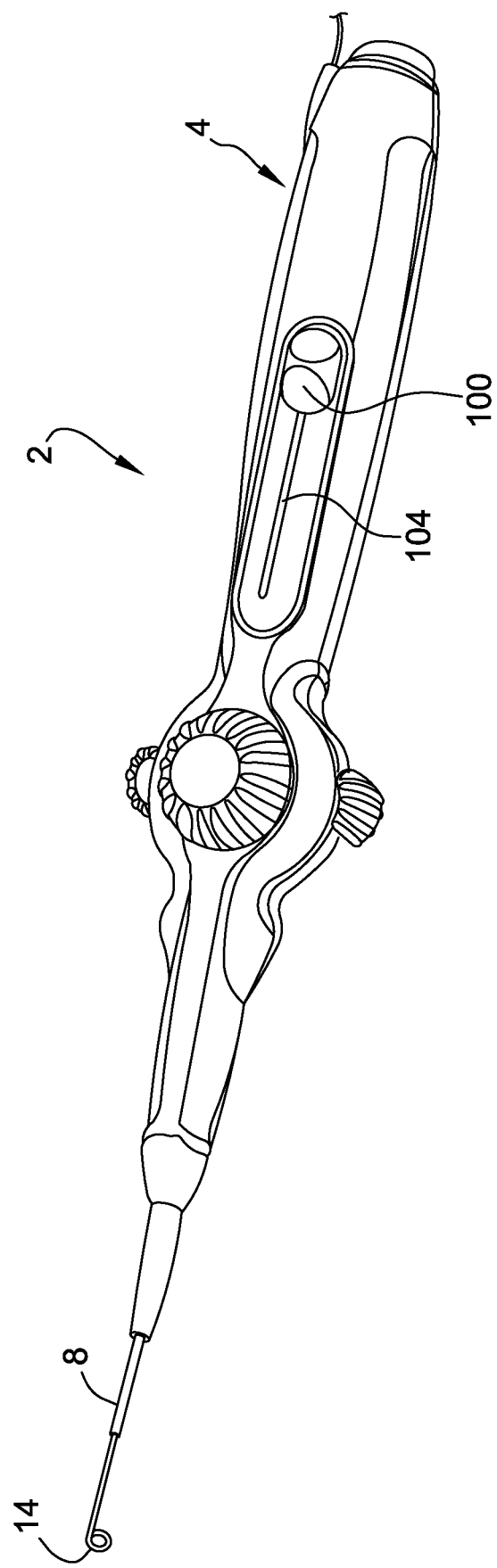
FIG. 10 is an isometric view of a catheter including a sliding mechanism for adjusting the diameter of a loop member on the catheter shaft.

In an alternative embodiment of the present disclosure, the catheter (and hence the catheter handle) may include a sliding mechanism coupled to a gear assembly in place of the sliding member and rotating knob combination described above to allow for adjustment of the diameter of the loop member. This sliding mechanism and gear assembly work in a similar manner as described above with respect to the sliding member and rotating knob to create a tension on a loop member pull wire to adjust the diameter of the loop member. With this embodiment, the sliding mechanism, which is engaged with the gear assembly, is moved in a proximal-distal direction (with reference to the catheter handle) to adjust the diameter of the loop member, as opposed to the rotation action as described above for the sliding member and rotating knob. Referring now to FIG. 10 there is shown one embodiment of a bidirectional catheter 2 including catheter handle 4 and catheter shaft 8, including loop member 14. Bidirectional catheter 2 additionally includes sliding mechanism 100 located in track 104. Sliding mechanism 100 controls the diameter adjustment of loop member 14, as further illustrated in FIG. 11. Sliding mechanism 100 will generally include teeth or gears (not shown in FIG. 11) to suitably engage a gear assembly or member (not shown in FIG. 10, but see FIG. 11) located in the catheter handle and described herein.

Figure 11:
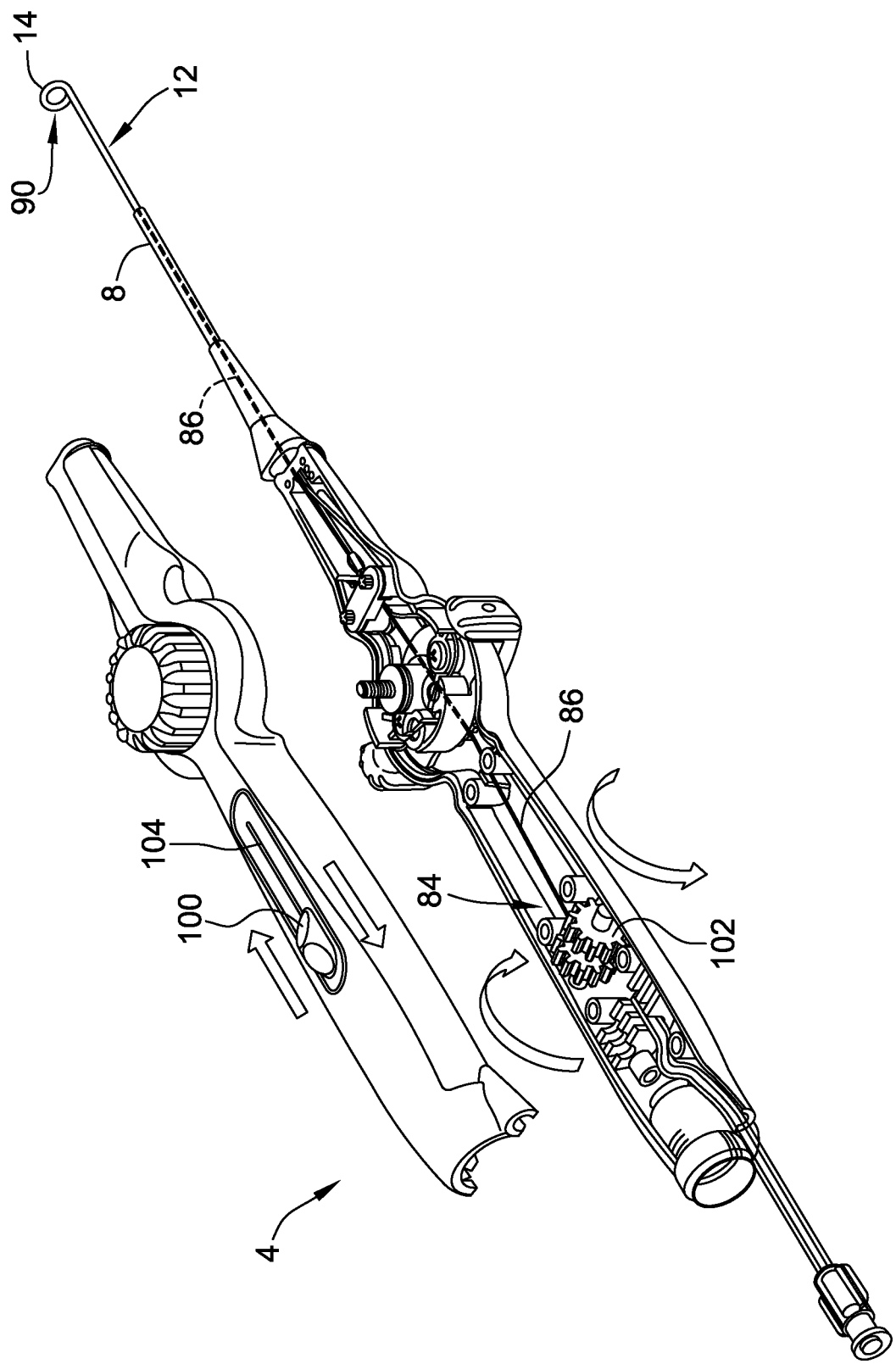
FIG. 11 is an isometric view of the catheter of FIG. 10 with the upper handle housing exploded away from the handle to reveal internal components.

FIG. 11 is a further illustration of the bidirectional catheter of FIG. 10. FIG. 11 shows sliding mechanism 100 in track 104 on catheter handle 4, and gear assembly 102, which is sized and configured to sit inside catheter handle 4 and engage sliding mechanism 100. As sliding mechanism 100 is moved along the arrows of FIG. 11 in track 104, gear assembly 102 also rotates along the same direction, as illustrated. Gear assembly 102 is connected to proximal portion 84 of loop member pull wire 86 and a distal portion 90 of loop member pull wire 86 is connected to an attachment point (not shown) in loop member 14 located on distal end deflectable portion 12 such that gear assembly 102 can control the diameter adjustment of loop member 14 as described herein when rotated by sliding mechanism 100. In some embodiments as described herein, the sliding mechanism and/or the gear assembly may further include a friction member thereon as described above to provide a "locking mechanism" such that the loop member may be placed into a desired conformation (i.e., a desired amount of diameter) and held there after the sliding mechanism is released; that is, the sliding mechanism may be released and the conformation of the loop member will be held until a further force is placed on the sliding mechanism to overcome the locking provided by the friction member.

Figure 12:
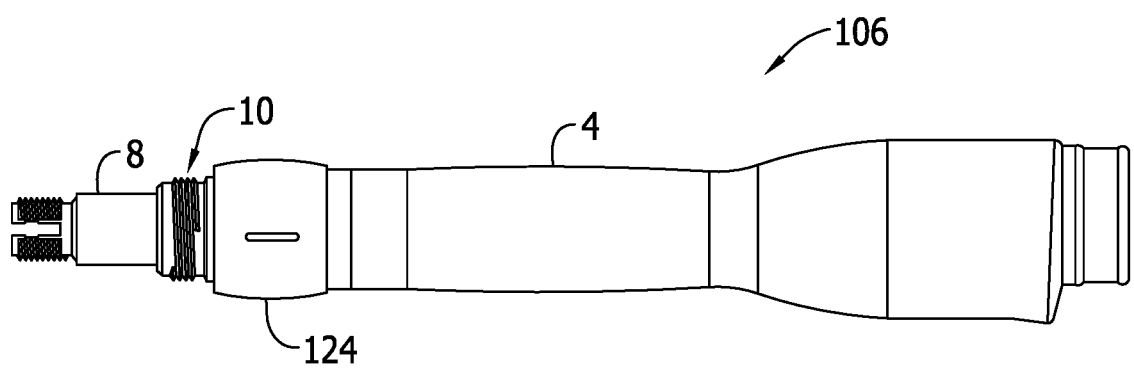
FIG. 12 is a side view of a portion of an alternative embodiment of a catheter.

Referring to FIG. 12, there is shown a view of an alternative embodiment of a catheter 106. Catheter 106 may be similar to catheter 2 shown in FIGS. 1-11, and like numerals are used to refer to elements of catheters 2 and 106. In some embodiments, catheter 106 is embodied as a unidirectional catheter, while in other embodiments, catheter 106 is embodied as a bidirectional catheter. In the illustrated embodiment, catheter 106 includes a longitudinally-extending catheter shaft 8 including proximal end portion 10 and distal end deflectable portion 12 (not shown in FIG. 12). Catheter 106 further includes a handle 4 coupled to proximal end portion 10, handle 4 including a rotatable knob 124. As shown and described with respect to FIGS. 1-11, distal end deflectable portion 12 includes loop member 14 (not shown in FIG. 12).

Figure 13:
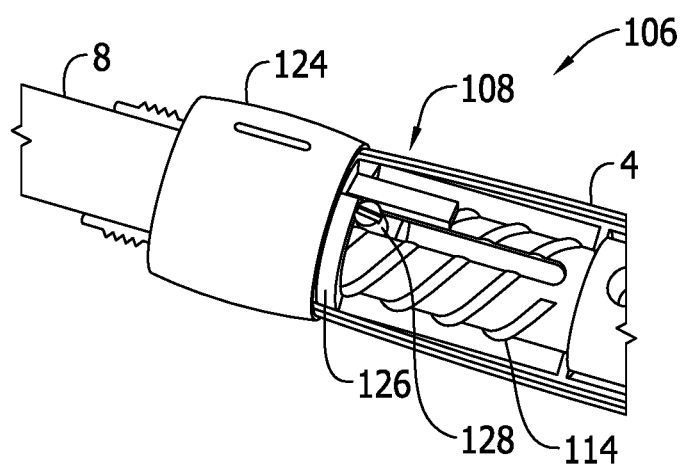
FIG. 13 is a partial cut-away, internal view of the catheter shown in FIG. 12.

FIG. 13 shows a partial cut-away, internal view of catheter 106. Catheter 106 includes a loop member adjustment mechanism 108 associated with handle 4 as well as a deflection mechanism (not shown) for deflecting distal end deflectable portion 12 (not shown) of catheter shaft 8. The deflection mechanism of catheter 106 may be substantially similar to the deflection mechanism(s) described above with respect to catheter 2 (e.g., steering actuator 6). Loop member adjustment mechanism 108 includes a loop member pull wire (not shown in FIG. 13), which may be similar to loop member pull wire 86, for adjusting the diameter of loop member 14. Loop member adjustment mechanism 108 includes knob 124, an inner actuator 126, a sliding member 128, and a rod member 114 as shown in detail in FIGS. 14-17.

Knob 124 is sized and configured to couple to inner actuator 126, such that rotation of knob 124 effects rotation of inner actuator 126. As described further herein, inner actuator 126 is configured to interface with rod member 114 such that rotational movement of inner actuator 126 is converted into linear, translational movement of inner actuator 126 parallel to a longitudinal axis of handle 4. In turn, the linear movement of inner actuator 126 drives linear, translational movement of sliding member 128. In the example embodiment, the loop member pull wire is coupled to sliding member 128, such that proximal translation of sliding member 128 increases tension in the loop member pull wire to reduce the diameter of loop member 14. Likewise, distal translation of sliding member 128 decreases tension in the loop member pull wire to increase the diameter of loop member 14.

Figure 14:
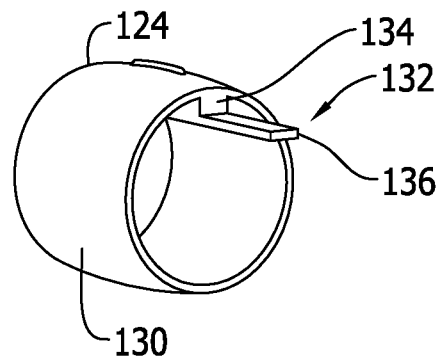
FIG. 14 illustrates a knob that may be used with the catheter shown in FIG. 12.
Figure 18:
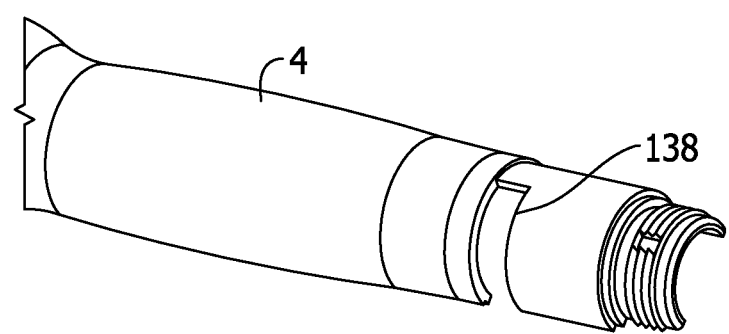
FIG. 18 is another partial cut-away, internal view of the catheter shown in FIG. 12.

Turning to FIG. 14, rotatable knob 124 is shown in greater detail. Rotatable knob 124 includes an annular body 130. Body 130 may be integrally formed as a single piece, or may be formed from two pieces coupled together. Rotatable knob 124 further includes an extension 132 extending from body 130. Extension 132 includes a radial arm 134 extending radially inward from body 130 as well as an axial arm 136 extending axially from radial arm 134. As shown in FIG. 18, handle 4 includes a cutout 138 defined therein. Handle cutout 138 provides a track for movement of radial arm 134 as knob 124 is rotated. Cutout 138 serves to limit the rotation of knob 124 within a predefined angular defined thereby. As described further herein, axial arm 136 engages with inner actuator 126 to facilitate rotation of inner actuator 126 within handle 4.

Figure 15:
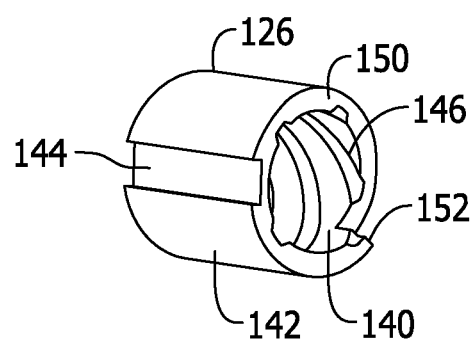
FIG. 15 illustrates an inner actuator that may be used with the catheter shown in FIG. 12.

Turning to FIG. 15, inner actuator 126 is shown in greater detail. In the illustrated embodiment, inner actuator 126 includes an inner surface 140 and an outer surface 142. Outer surface 142 includes a groove or cutout 144 defined therein. In the illustrated embodiment, cutout 144 receives axial arm 136 of knob extension 132. Accordingly, inner actuator 126 is operatively coupled to knob 124 such that rotational movement of knob 124 drives rotation of inner actuator 126. In addition, inner surface 140 of inner actuator 126 includes an interior threaded portion 146. As described further herein, interior threaded portion 146 interfaces with an exterior threaded portion of rod member 114. The threaded portions interface such that, as inner actuator 126 is rotated (i.e., as knob 124 is rotated), inner actuator 126 not only rotates but also translates linearly. Inner actuator 126 further includes an end wall 150 at a proximal end thereof. As described further herein, end wall 150 is configured to engage with at least a portion of sliding member 128, such that as inner actuator 126 moves linearly, inner actuator 126 drives sliding member 128 to move linearly as well. In the illustrated embodiment, end wall 150 has a helical profile, which functions to limit rotational movement of inner actuator 126 by providing a stop 152 that abuts sliding member 128.

Figure 16:
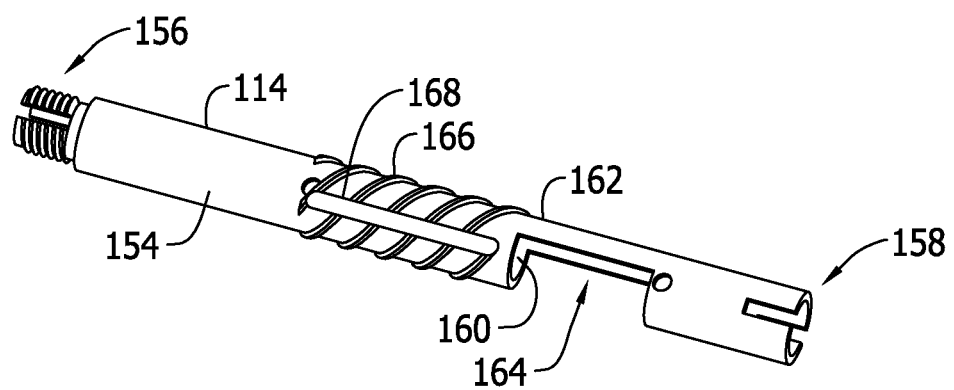
FIG. 16 illustrates a rod member that may be used with the catheter shown in FIG. 12

Rod member 114 is shown in greater detail in FIG. 16. In the illustrated embodiment, rod member 114 includes a body 154 extending between a distal end 156 and a proximal end 158. In the example embodiment, rod member 114 is longitudinally oriented within handle 4. More specifically, in some embodiments, rod member 114 is substantially coaxial with handle 4. In other embodiments, rod member 114 may be other than coaxial with handle 4, however, preferably, rod member 114 extends parallel to a longitudinal axis of handle 4. Body 154 is substantially cylindrical and, in the illustrated embodiment, substantially hollow, such that rod member 114 includes an inner surface 160 and an outer surface 162. Inner surface 160 defines a channel 164 extending through body 154. Outer surface 162 includes an exterior threaded portion 166. As described above, exterior threaded portion 166 engages interior threaded portion 146 of inner actuator 126 to convert rotational movement of inner actuator 126 into linear movement thereof. In addition, rod member 114 includes a longitudinally extending slot 168 defined therein. As described further herein, channel 164 and slot 168 guide and limit movement of sliding member 128 relative to rod member 114.

Figure 17:
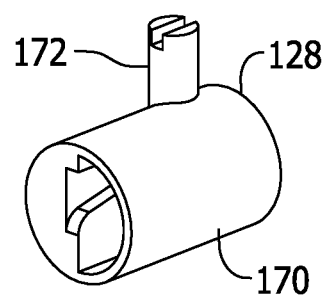
FIG. 17 illustrates a sliding member that may be used with the catheter shown in FIG. 12

Sliding member 128 is illustrated in greater detail in FIG. 17. In the illustrated embodiment, sliding member 128 includes a substantially cylindrical body 170. Body 170 is sized such that body 170 is positionable and moveable within channel 164 of rod member 114. In addition, sliding member 128 includes a tension adjustment pin 172 extending radially from body 170. The loop member pull wire is anchored to tension adjustment pin 172, which may be substantially similar to tension adjustment pin 88. In the example embodiment, tension adjustment pin 172 extends radially outward through slot 168 of rod member 114. In addition, tension adjustment pin 172 engages end wall 150 of inner actuator 126. As inner actuator 126 moves linearly with respect to handle 4, end wall 150, coupled to tension adjustment pin 172, forces corresponding movement of sliding member 128. Because inner actuator 126 also rotates, slot 168 ensures that tension adjustment pin 172 is not rotated but only moves linearly, thereby guiding and limiting the movement of tension adjustment pin 172, and, accordingly, sliding member 128. Sliding member 128 slides or translates within channel 164 of rod member 114.

Figure 19:
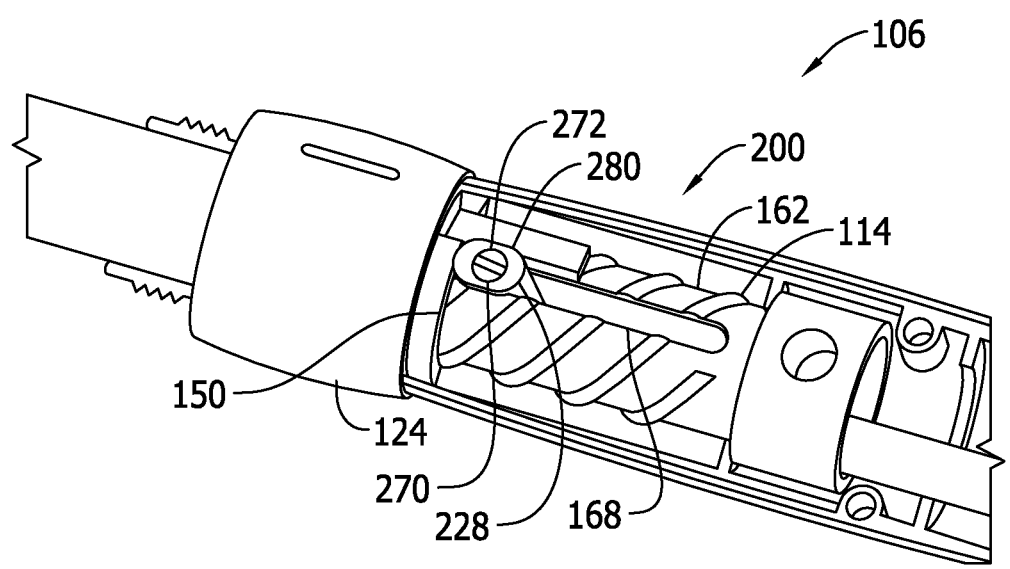
FIG. 19 is a partial cut-away, interior view of an alternative embodiment of the catheter shown in FIG. 12.

FIG. 19, shows a partial cut-away, interior view of an alternative embodiment of catheter 106 shown in FIG. 12. In the illustrated embodiment, a loop member adjustment mechanism 200 includes many of the same elements as shown and described with respect to FIGS. 12-18. However, loop member adjustment mechanism 200 includes a sliding member 228 instead of sliding member 128. Sliding member 228 includes a body 270. Body 270 is substantially rod shaped and extends perpendicular to rod member 114. In the illustrated embodiment, body 270 has an oval shape. Body 270 includes a flange or lip 280 configured to couple with outer surface 162 of rod member 114, such that sliding member 228 remains seated within slot 168. Sliding member 228 also includes a tension adjustment pin 272 substantially coaxial with body 270, tension adjustment pin 272 anchoring the loop member pull wire to sliding member 228. In this embodiment, loop member adjustment mechanism 200 functions substantially similarly to loop member adjustment mechanism 108, in that inner actuator 126 is configured to push sliding member 228 in a linear direction, increasing or decreasing tension in the loop member pull wire to adjust the loop diameter. However, in this embodiment, end wall 150 of inner actuator 126 engages body 270 (including lip 280) of sliding member 228.

Figure 20:
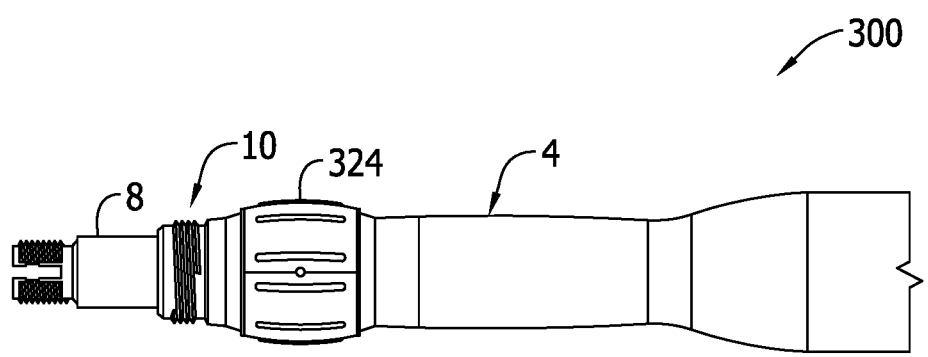
FIG. 20 is a side view of a portion of an alternative embodiment for a catheter.
Figure 21:
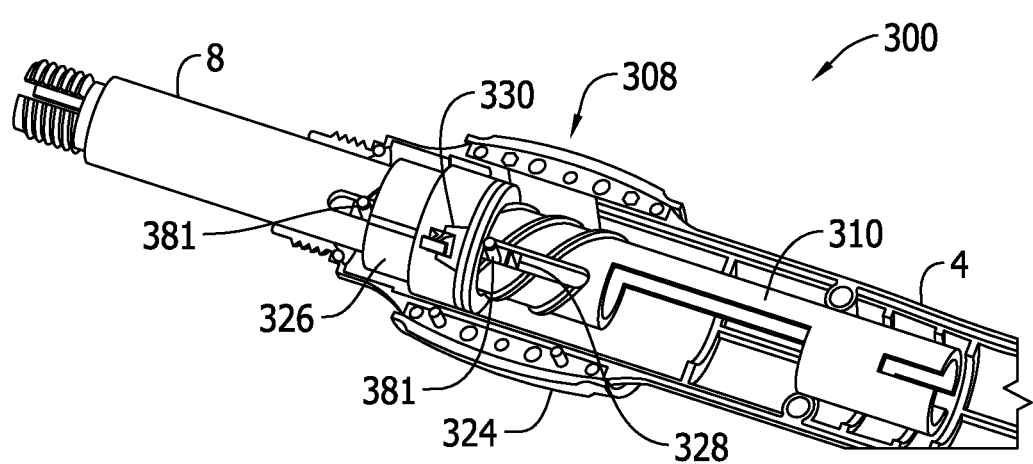
FIG. 21 is a partial cut-away, internal view of the catheter shown in FIG. 20.
Figure 22:
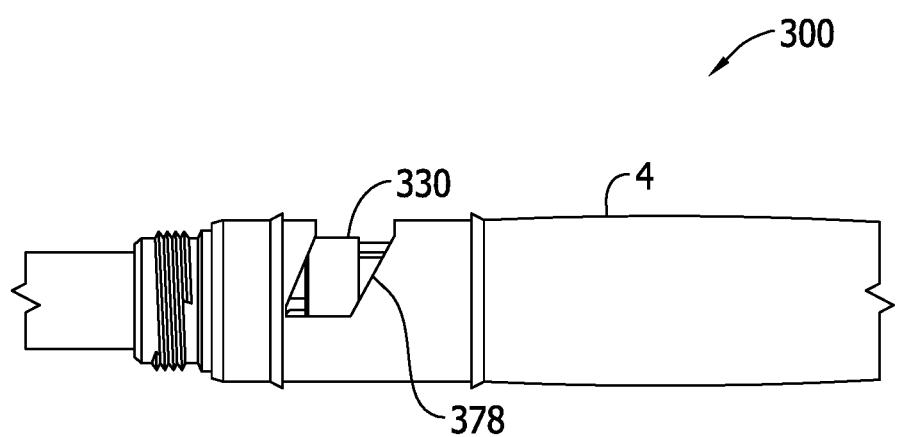
FIG. 22 is another partial cut-away view of the catheter shown in FIG. 20.

FIGS. 20-27 illustrate another alternative embodiment of a catheter 300. Specifically, FIG. 20 illustrates a side view of a portion of catheter 300, FIG. 21 is a partial cut-away, internal view of catheter 300, and FIG. 22 is another partial cut-away view of catheter 300. FIGS. 23-27 illustrate various elements of catheter 300 in greater detail. Catheter 300 may be similar to catheter 2 shown in FIGS. 1-11, and like numerals are used to refer to elements of catheters 2 and 300. In some embodiments, catheter 300 is embodied as a unidirectional catheter, while in other embodiments, catheter 300 is embodied as a bidirectional catheter. In the illustrated embodiment, catheter 300 includes a longitudinally-extending catheter shaft 8 including proximal end portion 10 and distal end deflectable portion 12 (not shown in FIG. 20). Catheter 300 further includes a handle 4 coupled to proximal end portion 10, handle 4 including a rotatable knob 324. As shown and described with respect to FIGS. 1-11, distal end deflectable portion 12 includes loop member 14 (not shown in FIG. 20).

Catheter 300 includes a loop member adjustment mechanism 308 associated with handle 4 as well as a deflection mechanism (not shown) for deflecting distal end deflectable portion 12 of catheter shaft 8. The deflection mechanism of catheter 300 may be substantially similar to the deflection mechanism(s) described above with respect to catheter 2 (e.g., steering actuator 6). Loop member adjustment mechanism 308 includes a loop member pull wire (not shown in FIGS. 20-28), which may be similar to loop member pull wire 86, for adjusting the diameter of loop member 14. Loop member adjustment mechanism 308 includes knob 324, a sliding ring 330, an inner actuator 326, a sliding member 328, and a rod member 310, as shown in detail in FIGS. 23-27.

Knob 324 is sized and configured to couple to sliding ring 330, and sliding ring 330 is sized and configured to couple to inner actuator 326, such that rotation of knob 324 effects rotation of sliding ring 330 and, accordingly, of inner actuator 326. As described further herein, inner actuator 326 is configured to interface with rod member 310 such that rotational movement of inner actuator 326 is converted into linear, translational movement of inner actuator 326 parallel to a longitudinal axis of handle 4. In turn, the linear movement of inner actuator 326 drives linear, translational movement of sliding member 328. In the example embodiment, the loop member pull wire is coupled to sliding member 328, such that proximal translation of sliding member 328 increases tension in the loop member pull wire to reduce the diameter of loop member 14. Likewise, distal translation of sliding member 328 decreases tension in the loop member pull wire to increase the diameter of loop member 14.

Figure 23:
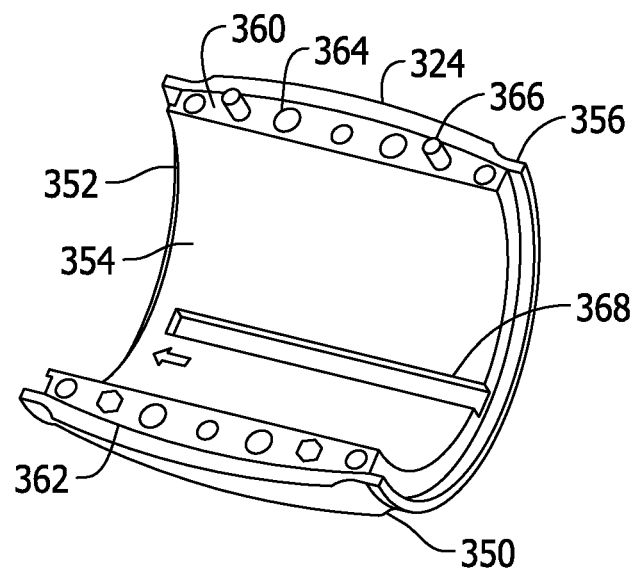
FIG. 23 illustrates a knob that may be used with the catheter shown in FIG. 20.

Turning to FIG. 23, rotatable knob 324 is a two-piece knob 324 that includes a first piece or first half 350 and second half or second piece (not shown) that is substantially a mirror image of first half 350. First half 350 includes a semi-annular body 352 that defines an inner surface 354 and an outer surface 356. As described herein, outer surface 356 may include a grip material or other material to improve frictional engagement with and/or comfort in handling of knob 324. First half 350 further includes a first edge 360 and a second edge 362 that engage a corresponding first and second edge of the second half of knob 324, when knob 324 is constructed. In the illustrated embodiment, each of first edge 360 and second edge 362 includes at least one pin hole 364 defined therein and at least one pin 366 extending therefrom. In some embodiments, first edge 360 and/or second edge 362 may include only pin holes 364 or only pins 366. Each pin hole 364 on one of the first piece 350 and the second piece is configured to receive a corresponding pin 366 therein, that pin 366 extending from the other of the first piece 350 and the second piece, to couple first piece 350 to the second piece. Pins 366 may be any type of pin suitable for coupling the pieces of knob 324 together, including, but not limited to, crush pins and/or alignment pins. The pieces of knob 324 may additionally or alternatively be coupled together using other suitable coupling elements, such as adhesive, hinge(s), and/or other fasteners than pins 366. First piece 350 further includes at least one groove 368 defined in inner surface 354. As described further herein, groove 368 is configured to engage with at least a portion of sliding ring 330 to drive rotation of sliding ring 330 as knob 324 is rotated.

Figure 24:
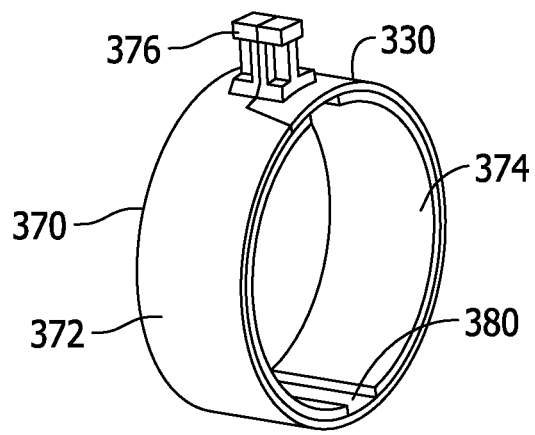
FIG. 24 illustrates a sliding ring that may be used with the catheter shown in FIG. 20.

FIG. 24 illustrates sliding ring 330 in greater detail. In the illustrated embodiment, sliding ring 330 includes an annular body 370 defining an outer surface 372 and an inner surface 374. Sliding ring 330 further includes a protrusion or tab 376 extending radially outwardly from outer surface 372. Tab 376 engages groove 368 (shown in FIG. 23) of knob 324 to couple sliding ring 330 to knob 324. As shown in FIG. 22, handle 4 includes a cutout 378 defined therein. Handle cutout 378 provides a track for movement of tab 376 as knob 324 is rotated and serves to limit the rotation of knob 324 within a predefined angle defined thereby. Sliding ring 330 also includes at least one groove or cutout 380 defined in inner surface 374. As described further herein, cutouts 380 are configured to engage with at least a portion of inner actuator 326 to drive rotation of inner actuator 326 as knob 324 (and, therefore, sliding ring 330) is rotated.

Figure 25:
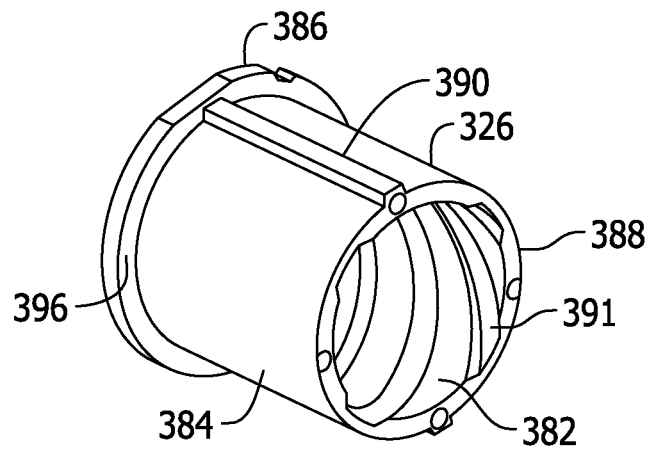
FIG. 25 illustrates an inner actuator that may be used with the catheter shown in FIG. 20.

FIG. 25 illustrates inner actuator 326 in greater detail. In the illustrated embodiment, inner actuator 326 includes an inner surface 382 and an outer surface 384, as well as a proximal end 386 and a distal end 388. Outer surface 384 includes at least one protrusion or ridge 390 extending therefrom. Each ridge 390 engages with a corresponding cutout 378 (shown in FIG. 24) of sliding ring 330 to couple inner actuator 326 to sliding ring 330. Accordingly, inner actuator 326 is operatively albeit indirectly coupled to knob 324 such that rotational movement of knob 324 drives rotation of inner actuator 326. In addition, inner surface 382 of inner actuator 326 includes an interior threaded portion 391. As described further herein, interior threaded portion 391 interfaces with an exterior threaded portion of rod member 310. The threaded portions interface such that, as inner actuator 326 is rotated (i.e., as knob 324 is rotated), inner actuator 326 not only rotates but also translates linearly. Inner actuator 326 further includes a radially extending annular flange 396 at proximal end 386 thereof. Flange 396 engages with sliding ring 330 to restrict proximal movement of sliding ring 330 and prevent sliding ring 330 from disengaging from inner actuator 326.

Figure 26:
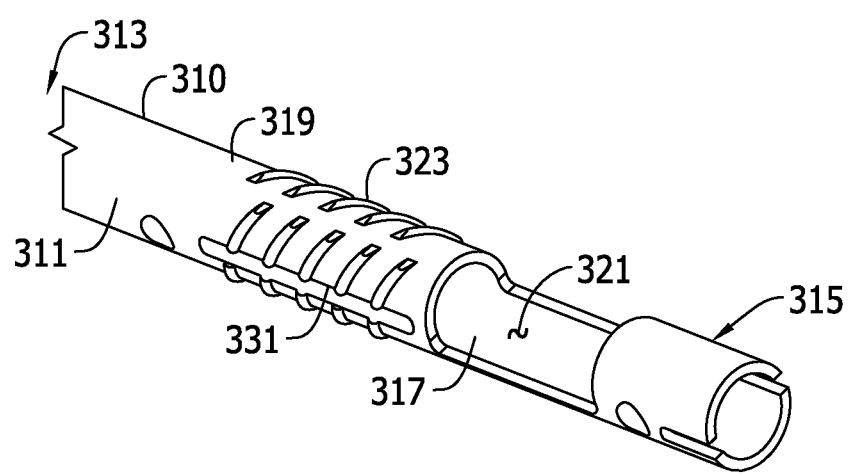
FIG. 26 illustrates a rod member that may be used with the catheter shown in FIG. 20.

Rod member 310 is shown in greater detail in FIG. 26. In the illustrated embodiment, rod member 310 includes a body 311 extending between a distal end 313 and a proximal end 315. In the example embodiment, rod member 310 is longitudinally oriented within handle 4. More specifically, in some embodiment, rod member 310 is substantially coaxial with handle 4. In other embodiments, rod member 310 may be other than coaxial with handle 4, however, preferably, rod member 310 extends parallel to a longitudinal axis of handle 4. Body 311 is substantially cylindrical and, in the illustrated embodiment, substantially hollow, such that rod member 310 includes an inner surface 317 and an outer surface 319. Inner surface 317 defines a channel 321 extending through body 311. Outer surface 319 includes an exterior threaded portion 323. As described above, exterior threaded portion 323 engages interior threaded portion 391 of inner actuator 326 to convert rotational movement of inner actuator 326 into linear movement thereof. In addition, rod member 310 includes a longitudinally extending slot 331 defined therein. As described further herein, channel 321 and slot 331 guide and limit movement of sliding member 328 relative to rod member 310.

Figure 27:
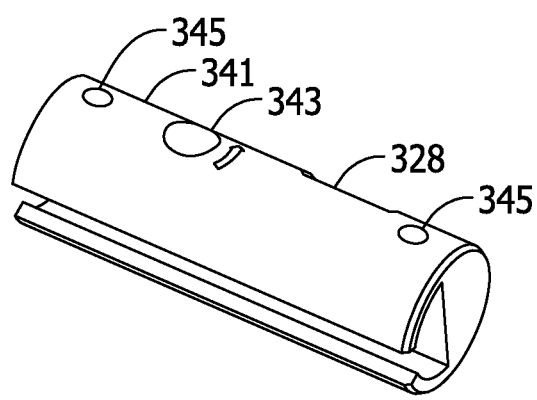
FIG. 27 illustrates a sliding member that may be used with the catheter shown in FIG. 20.

Sliding member 328 is illustrated in greater detail in FIG. 27. In the illustrated embodiment, sliding member 328 includes a substantially cylindrical body 341. Body 341 is sized such that body 341 is positionable and moveable within channel 321 of rod member 310. In addition, sliding member 328 includes a tension pin seat 343 configured to receive a tension adjustment pin (not shown). The loop member pull wire is anchored to the tension adjustment pin, which may be substantially similar to tension adjustment pin 88. Sliding member 328 further includes distal and proximal pin seats 345 configured to receive dowel pins 381 (shown in FIG. 21) therein. Dowel pins 381 engage proximal and distal ends 386, 388 of inner actuator 326 to operatively couple sliding member 328 to inner actuator 326. As inner actuator 326 moves linearly with respect to handle 4, dowel pins 381, coupled proximal and distal ends 386, 388 of inner actuator 326, force corresponding movement of sliding member 328. Because inner actuator 326 also rotates, slot 331 ensures that dowel pins 381 are not rotated but are restricted to linear motion, thereby guiding and limiting the movement of dowel pins 381 and, accordingly, sliding member 328. Sliding member 328 slides or translates within channel 321 of rod member 310.

Figure 28:
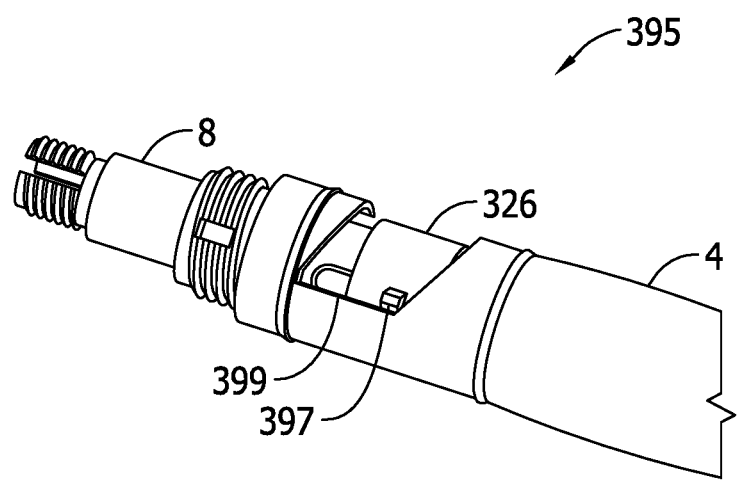
FIG. 28 is a partial cut-away view of an alternative embodiment of the catheter shown in FIG. 20.

FIG. 28 shows an alternative embodiment of a catheter 395. Catheter 395 may be substantially similar to catheter 106 as shown in FIGS. 20-27. In this embodiment, however, catheter 395 does not include sliding ring 330 (shown in FIGS. 20 and 24). Rather, inner actuator 326 of loop member adjustment mechanism 308 is configured to interface directly with knob 324. Accordingly, inner actuator 326 includes a tab 397 as opposed to ridges 390 (shown in FIG. 25), wherein tab 397 engages groove 368 (shown in FIG. 23) of knob 324. As such, a cutout 399 defined in handle 4 is configured to limit rotation of inner actuator 326 by restricting angular rotation of tab 397. Handle cutout 399 may be larger than handle cutout 378 (shown in FIG. 22) in some embodiments and/or may permit greater or less angular rotation of knob 324.

Figure 29:
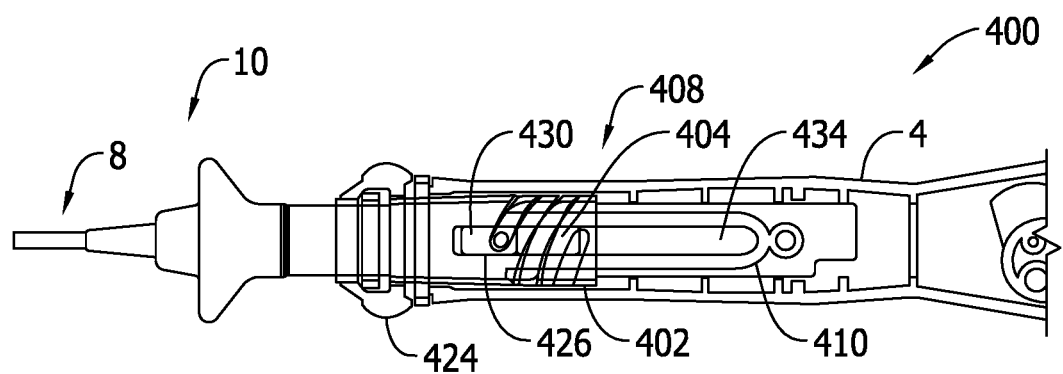
FIG. 29 is an internal view of another embodiment of a catheter in an unactuated configuration.
Figure 30:
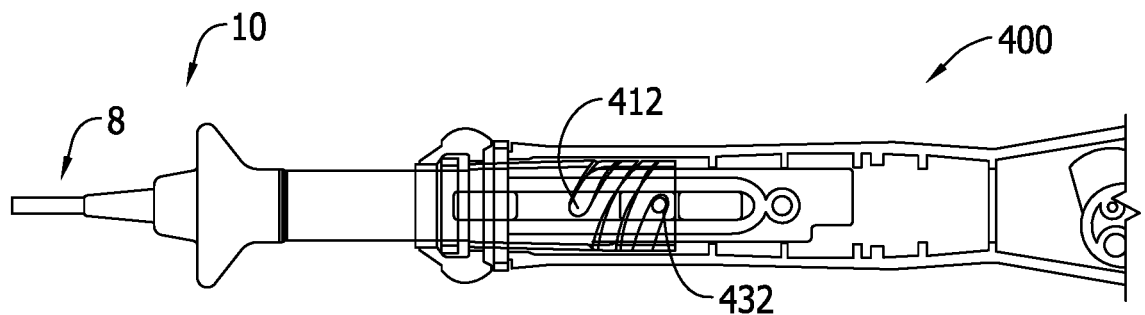
FIG. 30 is an internal view of the catheter shown in FIG. 29 in an actuated configuration.

FIGS. 29 and 30 illustrate another embodiment of a catheter 400. Specifically, FIG. 29 is an internal view of catheter 400 in an unactuated configuration, and FIG. 30 is an internal view of catheter 300 in an actuated configuration. Catheter 300 may be similar to catheter 2 shown in FIGS. 1-11, catheter 106 shown in FIGS. 12-20, and/or catheter 300 shown in FIGS. 21-28, and like numerals are used to refer to elements of catheters 2, 106, 300, and 400. In some embodiments, catheter 400 is embodied as a unidirectional catheter, while in other embodiments, catheter 400 is embodied as a bidirectional catheter. In the illustrated embodiment, catheter 400 includes a longitudinally-extending catheter shaft 8 including proximal end portion 10 and distal end deflectable portion 12 (not shown in FIGS. 29 and 30). Catheter 400 further includes a handle 4 coupled to proximal end portion 10, handle 4 including a rotatable knob or wheel 424. As shown and described with respect to FIGS. 1-11, distal end deflectable portion 12 includes loop member 14 (not shown in FIGS. 29 and 30).

Catheter 400 includes a loop member adjustment mechanism 408 associated with handle 4 and may further include a deflection mechanism (not shown in FIGS. 29 and 30) for deflecting distal end deflectable portion 12 of catheter shaft 8. The deflection mechanism of catheter 400 may be substantially similar to the deflection mechanism(s) described above with respect to catheter 2 (e.g., steering actuator 6). Loop member adjustment mechanism 408 includes a loop member pull wire (not shown in FIGS. 29 and 30), which may be similar to loop member pull wire 86, for adjusting the diameter of loop member 14. Loop member adjustment mechanism 408 includes wheel 424, a tube member 402, an inner actuator 426, a lug member 404, and a rod member 410.

Wheel 424 is coupled to tube member 402, such that rotation of wheel 424 also rotates tube member 402. Tube member 402 is substantially cylindrical, and includes a helix cutout 412 configured to engage at least a portion of inner actuator 426, such that rotational movement of tube member 402 moves or pushes the inner actuator 426 in a linear or longitudinal direction along rod member 410. More specifically, inner actuator 426 includes a body 430 and a protrusion 432 extending radially outward from body 430. Body 430 is sized and configured to slide within a channel or slot 434 defined in rod member 410. Protrusion 432 engages helical cutout 412, such that as tube member 402 is rotated (i.e., wheel 424 is rotated), helical cutout 412 converts rotational movement of tube member 402 into longitudinal movement of inner actuator 426 through rod member 410. In some embodiments, rod member 410 is translated distally, as shown in FIG. 30.

Lug member 404 is sized and configured to fit within rod member 410, proximal to inner actuator 426. Inner actuator 426 is further configured to interact with lug member 404, such that linear movement of inner actuator 426 moves or pushes lug member 404 longitudinally to increase tension in the loop member pull wire and thereby decrease a diameter of loop member 14. Slot 434 of rod member 410 limits further linear movement of lug member 404 after lug member 404 reaches a predetermined position, as shown in FIG. 30.

Figure 31:
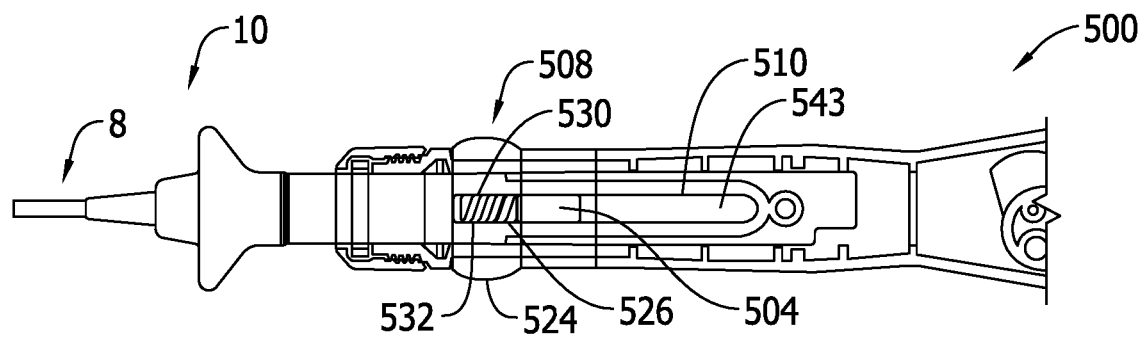
FIG. 31 is an internal view of another embodiment of a catheter in an unactuated configuration.
Figure 32:
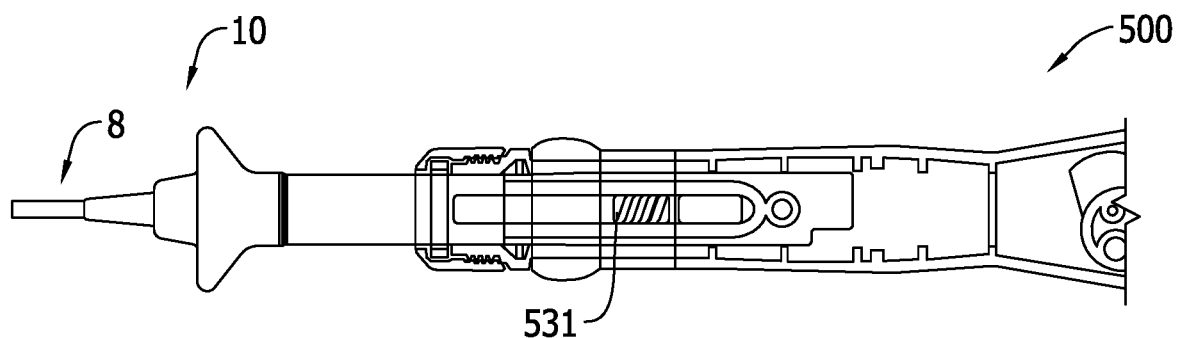
FIG. 32 is an internal view of the catheter shown in FIG. 31 in an actuated configuration.

FIGS. 31 and 32 illustrate another embodiment of a catheter 500. Specifically, FIG. 31 is an internal view of catheter 500 in an unactuated configuration, and FIG. 32 is an internal view of catheter 500 in an actuated configuration. Catheter 500 may be similar to catheter 2 shown in FIGS. 1-11, catheter 106 shown in FIGS. 12-20, catheter 300 shown in FIGS. 21-28, and/or catheter 400 shown in FIGS.

29-30, and like numerals are used to refer to elements of catheters 2, 106, 300, 400, and 500. In some embodiments, catheter 500 is embodied as a unidirectional catheter, while in other embodiments, catheter 500 is embodied as a bidirectional catheter. In the illustrated embodiment, catheter 500 includes a longitudinally-extending catheter shaft 8 including proximal end portion 10 and distal end deflectable portion 12 (not shown in FIGS. 31 and 32). Catheter 500 further includes a handle 4 coupled to proximal end portion 10, handle 4 including a rotatable knob or wheel 524. As shown and described with respect to FIGS. 1-11, distal end deflectable portion 12 includes loop member 14 (not shown in FIGS. 31 and 32).

Catheter 500 includes a loop member adjustment mechanism 508 associated with handle 4 and may further include a deflection mechanism (not shown in FIGS. 31 and 32) for deflecting distal end deflectable portion 12 of catheter shaft 8. The deflection mechanism of catheter 500 may be substantially similar to the deflection mechanism(s) described above with respect to catheter 2 (e.g., steering actuator 6). Loop member adjustment mechanism 508 includes a loop member pull wire (not shown in FIG. 30), which may be similar to loop member pull wire 86, for adjusting the diameter of loop member 14. Loop member adjustment mechanism 508 includes wheel 524, an inner actuator 526, a lug member 504, and a rod member 510.

Wheel 524 is operatively coupled to inner actuator 526 (e.g., via internal threads, not shown), such that rotation of wheel 524 also rotates inner actuator 526. Inner actuator 526 includes a body 530, which includes an outer surface 531 having an exterior threaded portion 532. Body 530 is sized and configured to slide within a channel or slot 534 defined in rod member 510. Exterior threaded portion 532 engages with wheel 524 (e.g., an interior threaded portion of wheel 524), such that as wheel 524 is rotated, inner actuator 526 is rotated and translated longitudinally through rod member 510. In some embodiments, rod member 510 is configured to translate distally, as shown in FIG. 32.

Lug member 504 is sized and configured to fit within rod member 510, proximal to inner actuator 526. Inner actuator 526 is further configured to interact with lug member 504, such that linear movement of inner actuator 526 moves or pushes lug member 504 longitudinally to increase tension in the loop member pull wire and thereby decrease a diameter of loop member 14. Slot 534 of rod member 510 limits further linear movement of lug member 504 after lug member 504 reaches a predetermined position, as shown in FIG. 32.

Figure 33:
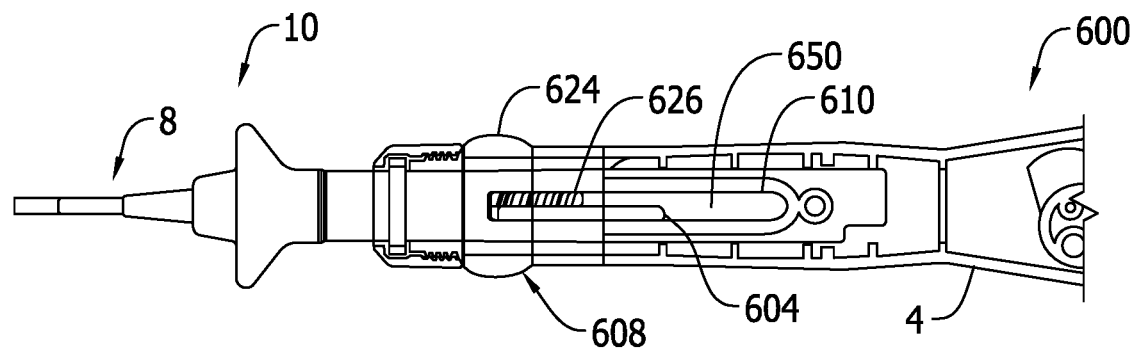
FIG. 33 is an internal view of another embodiment of a catheter in an unactuated configuration.
Figure 34:
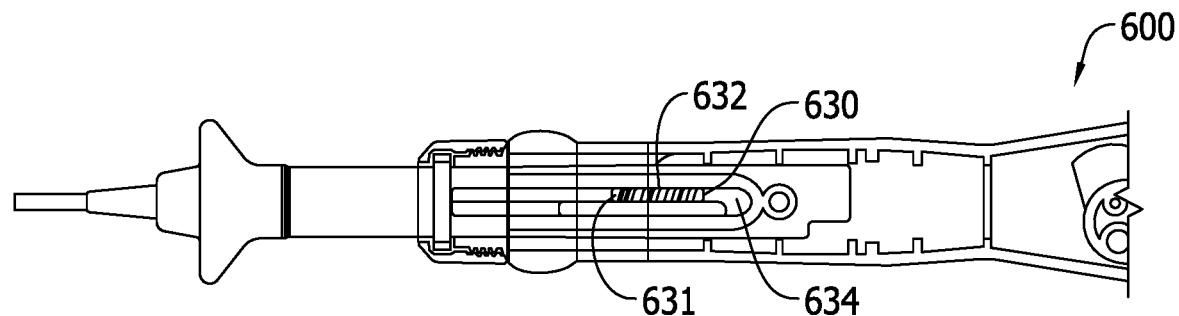
FIG. 34 is an internal view of the catheter shown in FIG. 33 in an actuated configuration

FIGS. 33 and 34 illustrate another embodiment of a catheter 600. Specifically, FIG. 33 is an internal view of catheter 600 in an unactuated configuration, and FIG. 34 is an internal view of catheter 600 in an actuated configuration. Catheter 600 may be similar to catheter 2 shown in FIGS. 1-11, catheter 106 shown in FIGS. 12-20, catheter 300 shown in FIGS. 21-28, catheter 400 shown in FIGS. 29 and 30, and/or catheter 500 shown in FIGS. 31 and 32, and like numerals are used to refer to elements of catheters 2, 106, 300, 400, 500, and 600. In some embodiments, catheter 600 is embodied as a unidirectional catheter, while in other embodiments, catheter 600 is embodied as a bidirectional catheter. In the illustrated embodiment, catheter 600 includes a longitudinally-extending catheter shaft 8 including proximal end portion 10 and distal end deflectable portion 12 (not shown in FIGS. 33 and 34). Catheter 600 further includes a handle 4 coupled to proximal end portion 10, handle 4 including a rotatable knob or wheel 624. As shown and described with respect to FIGS. 1-11, distal end deflectable portion 12 includes loop member 14 (not shown in FIG. 333).

Catheter 600 includes a loop member adjustment mechanism 608 associated with handle 4 and may further include a deflection mechanism (not shown in FIGS. 33 and 34) for deflecting distal end deflectable portion 12 of catheter shaft 8. The deflection mechanism of catheter 600 may be substantially similar to the deflection mechanism(s) described above with respect to catheter 2 (e.g., steering actuator 6). Loop member adjustment mechanism 608 includes a loop member pull wire (not shown in FIG. 33), which may be similar to loop member pull wire 86, for adjusting the diameter of loop member 14. Loop member adjustment mechanism 608 includes wheel 624, an inner actuator 626, a lug member 604, and a rod member 610.

Wheel 624 is operatively coupled to inner actuator 626 (e.g., via internal threads, not shown), such that rotation of wheel 624 also rotates inner actuator 626. Inner actuator 626 includes a body 630 which includes an outer surface 631 having an exterior threaded portion 632. Body 630 is sized and configured to slide within a channel or slot 650 defined in rod member 610. More specifically, in the illustrated embodiment, lug member 604 is extended longitudinally within slot 650, and inner actuator 626 is slideable within slot 650 alongside lug member 604. Exterior threaded portion 632 engages with wheel 624 (e.g., an interior threaded portion of wheel 624), such that as wheel 624 is rotated, inner actuator 626 is rotated and translated longitudinally through rod member 610. In some embodiments, rod member 610 is configured to be translated distally, as shown in FIG. 34.

Lug member 604 is sized and configured to fit within rod member 610, alongside inner actuator 626. Inner actuator 626 is further configured to interact (e.g., frictionally and/or otherwise) with lug member 604, such that linear movement of inner actuator 626 moves or pushes lug member 604 longitudinally to increase tension in the loop member pull wire and thereby decrease a diameter of loop member 14. Slot 650 of rod member 610 may limit further linear movement of lug member 604 after lug member 604 reaches a predetermined position, as shown in FIG. 34.

Figure 35:
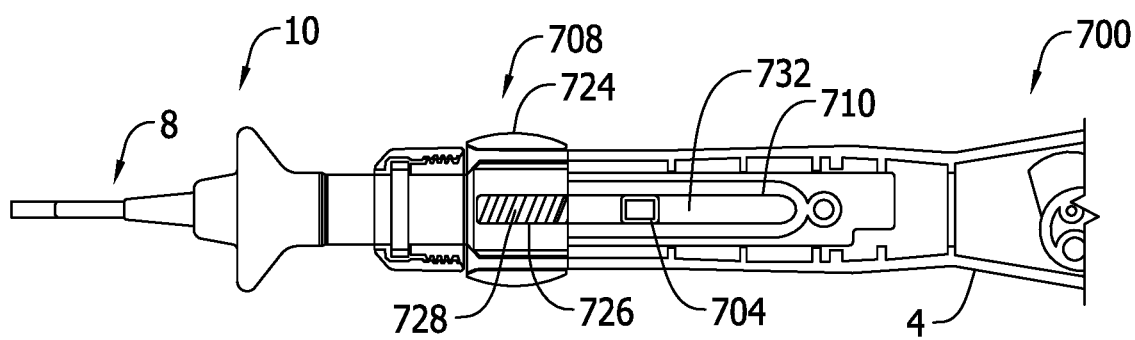
FIG. 35 is an internal view of another embodiment of a catheter in an unactuated configuration.
Figure 36:
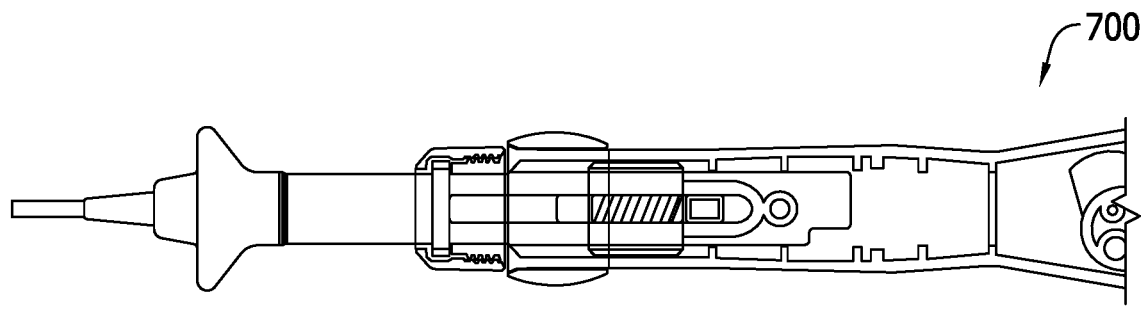
FIG. 36 is an internal view of the catheter shown in FIG. 35 in an actuated configuration.

FIGS. 35 and 36 illustrate another embodiment of a catheter 700. Specifically, FIG. 35 is an internal view of catheter 700 in an unactuated configuration, and FIG. 36 is an internal view of catheter 700 in an actuated configuration. Catheter 700 may be similar to catheter 2 shown in FIGS. 1-11, catheter 106 shown in FIGS. 12-20, catheter 300 shown in FIGS. 21-28, catheter 400 shown in FIGS. 29 and 30, catheter 500 shown in FIGS. 31 and 32, and/or catheter 600 shown in FIGS. 33 and 34, and like numerals are used to refer to elements of catheters 2, 106, 300, 400, 500, 600, and 700. In some embodiments, catheter 700 is embodied as a unidirectional catheter, while in other embodiments, catheter 700 is embodied as a bidirectional catheter. In the illustrated embodiment, catheter 700 includes a longitudinally-extending catheter shaft 8 including proximal end portion 10 and distal end deflectable portion 12 (not shown in FIGS. 35 and 36). Catheter 700 further includes a handle 4 coupled to proximal end portion 10, handle 4 including a rotatable knob or wheel 724. As shown and described with respect to FIGS. 1-11, distal end deflectable portion 12 includes loop member 14 (not shown in FIGS. 35 and 36).

Catheter 700 includes a loop member adjustment mechanism 708 associated with handle 4 and may further include a deflection mechanism (not shown in FIGS. 35 and 36) for deflecting distal end deflectable portion 12 of catheter shaft 8. The deflection mechanism of catheter 700 may be substantially similar to the deflection mechanism(s) described above with respect to catheter 2 (e.g., steering actuator 6). Loop member adjustment mechanism 708 includes a loop member pull wire (not shown in FIG. 35), which may be similar to loop member pull wire 86, for adjusting the diameter of loop member 14. Loop member adjustment mechanism 708 includes wheel 724, an inner actuator 726, a lug member 704, and a rod member 710.

In the illustrated embodiment, wheel 724 includes an interior threaded portion (not shown) that interfaces with an exterior threaded portion 728 of inner actuator 726. The interaction of these threaded portions converts rotational movement of wheel 724 into longitudinal movement of inner actuator 726.

Lug member 704 is sized and configured to fit within rod member 710, proximal to inner actuator 726. Inner actuator 726 is further configured to interact with lug member 704, such that linear movement of inner actuator 726 moves or pushes lug member 704 longitudinally to increase tension in the loop member pull wire and thereby decrease a diameter of loop member 14. Slot 732 of rod member 710 limits further linear movement of lug member 704 after lug member 704 reaches a predetermined position, as shown in FIG. 36.

In another embodiment of the present disclosure, the sliding member and/or the rotating knob of the bidirectional catheter as described in detail herein may be sized and configured to provide audible and/or tactile feedback to the user of the catheter at one or more desired times during use thereof. Feedback to the user may be provided, for example, regarding the angle of a turn of the catheter shaft or the loop size achieved. In one specific example, the sliding member may be sized and configured to provide an audible signal, such as a "clicking sound" to the user when a certain pre-determined loop diameter is achieved; that is, at the point that a pre-determined loop diameter is achieved by the user turning the rotating knob, a "clicking sound" is made by the sliding member so as to alert the user that is certain diameter has been reached. In addition to the "clicking sound" or in the alternative, for example, the sliding member and/or rotating knob may be sized and configured to provide a certain "mechanical tactile feel" once a certain pre-determined point is reached.

Other embodiments of the present disclosure include methods of using the catheters described herein, and particularly to using a bidirectional catheter including a means for adjusting the diameter of a loop member located on a distal portion of a catheter shaft. In one specific embodiment, a method of adjusting the diameter of a loop member located on a catheter shaft using a rotating knob located on the catheter handle and configured to engage a sliding member located interior the handle is disclosed. In this embodiment, the method comprises providing a catheter handle comprising (i) a deflection mechanism including a pull wire for deflecting a deflectable end distal portion of the catheter shaft; and (ii) a loop member pull wire for adjusting a diameter of the loop member, wherein a proximal end of the loop member pull wire is attached to a sliding member configured to interface with a rotating knob; and rotating the knob interfaced with the sliding member attached to the loop member pull wire to adjust the diameter of the loop member on the catheter shaft. In another embodiment, the method comprises providing a catheter handle comprising (i) a deflection mechanism including a pull wire for deflecting a deflectable end distal portion of the catheter shaft; and (ii) a loop member pull wire for adjusting a diameter of the loop member, wherein a proximal end of the loop member pull wire is attached to a sliding member configured to interface with a rotating knob; and translating the sliding member within the handle to adjust the diameter of the loop member on the catheter shaft. In some embodiments, the sliding member and/or the rotating knob may include a friction member to provide a "braking" or "locking" feature. As will be recognized by one skilled in the art based on the disclosure herein, the sliding mechanism and rotating knob in the above process could be replaced with the sliding mechanism and gear assembly as described herein to achieve the same result.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A catheter comprising:
   a longitudinally-extending catheter shaft comprising a proximal end portion and a distal end deflectable portion, wherein the distal end deflectable portion includes a loop member;
   a handle attached to the proximal end portion of the catheter shaft;
   a deflection mechanism positioned inside the handle and including a pull wire for deflecting the distal end deflectable portion of the catheter shaft; and
   a loop member adjustment mechanism for adjusting a diameter of the loop member, the loop member adjustment mechanism comprising:
      a single loop member pull wire, wherein a distal end of the single loop member pull wire is attached to the loop member;
      a sliding member, located within the handle, wherein the sliding member is configured to translate within the handle without rotating within the handle, wherein the sliding member comprises a first side including first gears, a second, opposite side including second gears, and a planar surface extending between the first side and the second side, and wherein a proximal end of the single loop member pull wire is directly coupled to a pin included in the sliding member, a portion of the single loop member pull wire extending across the planar surface of the sliding member; and a rotatable knob located on an exterior of the handle and circumscribing the sliding member, the rotatable knob interfacing with the sliding member such that rotation of the rotatable knob adjusts the diameter of the loop member by causing the sliding member, pin, and proximal end of the single loop member pull wire to translate within the handle, wherein to interface with the sliding member, an underside of the rotatable knob comprises third gears that engage both the first gears formed on the first side of the sliding member and the second gears formed on the second side of the sliding member.

2. The catheter of claim 1, wherein the sliding member is located proximally to the deflection mechanism with respect to the handle.

3. The catheter of claim 1, further comprising a locking mechanism for securing the single loop member pull wire in place after adjustment of the diameter of the loop member.

4. The catheter of claim 3, wherein the locking mechanism includes a threaded pitch of gears.

5. The catheter of claim 3, wherein the locking mechanism includes a friction ring.

6. The catheter of claim 3, wherein the locking mechanism includes a friction member positioned within a pocket defined in the first gears on the first side of the sliding member, the friction member sized to contact and interact with the third gears of the underside of the rotatable knob to facilitate securing the single loop member pull wire in place.

7. The catheter of claim 3, further comprising a distal locking ring located distal of the rotatable knob and a proximal locking ring located proximal of the rotatable knob.

8. The catheter of claim 1, wherein the sliding member includes at least one groove thereon sized and configured to slidably attach to a center guide channel positioned on the handle.

9. A deflecting and sizing apparatus for a catheter handle comprising a catheter shaft having a deflectable distal end portion including a loop member, the apparatus comprising:

a deflection mechanism positioned inside the handle and including a pull wire for deflecting the distal end deflectable portion of the catheter shaft; and a loop member adjustment mechanism for adjusting a diameter of the loop member, the loop member adjustment mechanism comprising:

a single loop member pull wire, wherein a distal end of the single loop member pull wire is attached to the loop member;

a sliding member, located within the handle, wherein the sliding member is configured to translate within the handle without rotating within the handle, wherein the sliding member comprises a first side including first gears, a second, opposite side including second gears, and a planar surface extending between the first side and the second side, and wherein a proximal end of the single loop member pull wire is directly coupled to a pin included in the sliding member, a portion of the single loop member pull wire extending across the planar surface of the sliding member; and a rotatable knob located on an exterior of the handle and circumscribing the sliding member, the rotatable knob interfacing with the sliding member such that rotation of the rotatable knob adjusts the diameter of the loop member by causing the sliding member, pin, and proximal end of the single loop member pull wire to translate within the handle, wherein to interface with the sliding member, an underside of the rotatable knob comprises third gears that engage both the first gears formed on the first side of the sliding member and the second gears formed on the second side of the sliding member.

10. The deflecting and sizing apparatus of claim 9, wherein the sliding member is located proximally to the deflection mechanism with respect to the handle.

11. The deflecting and sizing apparatus of claim 9, further comprising a locking mechanism for securing the single loop member pull wire in place after adjustment of the diameter of the loop member.

12. The deflecting and sizing apparatus of claim 11, wherein the locking mechanism includes a threaded pitch of gears.

* * * * *